United States Patent
Buchanan et al.

(10) Patent No.: US 6,479,467 B1
(45) Date of Patent: Nov. 12, 2002

(54) CYCLODEXTRIN ETHERS

(75) Inventors: Charles M. Buchanan, Kingsport, TN (US); Daniel W. Dixon, Jr., Church Hill, TN (US); Juanelle L. Lambert, Gray, TN (US); Ricky J. Offerman, Kingsport, TN (US); Matthew D. Wood, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/461,226

(22) Filed: Dec. 16, 1999

(51) Int. Cl.[7] .................. A61K 31/715; C08B 37/16
(52) U.S. Cl. .................. 514/58; 536/103; 536/124; 525/54.24
(58) Field of Search .................. 514/58; 536/103, 536/124; 525/54.24

(56) References Cited

U.S. PATENT DOCUMENTS

| | | | |
|---|---|---|---|
| 3,459,731 A | * 8/1969 | Gramera et al. | 260/209 |
| 4,722,815 A | 2/1988 | Shibanai | 264/117 |
| 4,727,064 A | 2/1988 | Pitha | 514/58 |
| 4,948,395 A | 8/1990 | Armstrong | 55/67 |
| 4,956,351 A | 9/1990 | Mesens et al. | 514/58 |
| 5,120,546 A | * 6/1992 | Hansen et al. | 424/449 |
| 5,492,947 A | * 2/1996 | Wood et al. | 524/48 |

FOREIGN PATENT DOCUMENTS

| JP | 58-108201 | 9/1983 |
|---|---|---|
| JP | 10-045609 | 2/1998 |

OTHER PUBLICATIONS

József Szejtli, "Chemistry, Physical and Biological Properties of Cyclodextrins", pp. 5–40 (date unknown).

* cited by examiner

Primary Examiner—James O. Wilson
Assistant Examiner—Leigh C. Maier
(74) Attorney, Agent, or Firm—Bernard J. Graves, Jr.; Michael J. Blake

(57) ABSTRACT

This invention relates to a new composition of matter which comprises hydroxybutenyl derivatives of cyclodextrins (HBenCD) or mixed ethers of cyclodextrins where at least one of the ether substituents is hydroxybutenyl (HBenRCD where R is an ether substituent other than hydroxybutenyl). This invention also relates to novel processes for the preparation of cyclodextrin ethers. This invention further relates to inclusion complexes formed between HBenCD or HBenRCD and guest molecules. Such inclusion complexes are useful in pharmaceutical, cosmetic, and food applications. Furthermore, this invention relates to the incorporation of HBenCD or HBenRCD or their inclusion complexes in thermoplastic materials, textiles or membranes.

54 Claims, 16 Drawing Sheets

Reaction of Cyclodextrins with EpB Resulting in Either Primary or Secondary Alcohols as Products.

Structure of α-, β-, and γ-Cyclodextrins.

Reaction of Cyclodextrins with EpB Resulting in Either Primary or Secondary Alcohols as Products.

MALDI-TOF Spectrum of Hydroxybutenyl-β-Cyclodextrin (HBen-β-CD) with MS of ca. 6.4.

MALDI-TOF Spectrum of Hydroxybutenyl-β-Cyclodextrin (HBen-β-CD) with MS of ca. 13.5.

Solubility isotherms of hydrocortisone in an aqueous media in the presence of MS 6.0 and 6.5 hydroxybutenyl-β-cyclodextrin (HBen-β-CD) and hydroxypropyl-β-cyclodextrin (HP-β-CD).

Calculation of apparent binding constants for hydrocortisone with MS 6.0 and 6.5 hydroxybutenyl-β-cyclodextrin (HBen-β-CD) and hydroxypropyl-β-cyclodextrin (HP-β-CD).

Solubility isotherms of ibuprofen in an aqueous media in the presence of MS 6.0 and 6.5 hydroxybutenyl-β-cyclodextrin (HBen-β-CD) and hydroxypropyl-β-cyclodextrin (HP-β-CD).

Calculation of apparent binding constants for ibuprofen with MS 6.0 and 6.5 hydroxybutenyl-β-cyclodextrin (HBen-β-CD) and hydroxypropyl-β-cyclodextrin (HP-β-CD).

Solubility isotherms of glibenclamide in an aqueous media in the presence hydroxybutenyl-β-cyclodextrin (HBen-β-CD) and hydroxypropyl-β-cyclodextrin (HP-β-CD).

Calculation of apparent binding constants for glibenclamide with hydroxybutenyl-β-cyclodextrin (HBen-β-CD) and hydroxypropyl-β-cyclodextrin (HP-β-CD).

Solubility isotherms of toluene in an aqueous media in the presence of hydroxybutenyl-β-cyclodextrin (HBen-β-CD) and hydroxypropyl-β-cyclodextrin (HP-β-CD).

Calculation of apparent binding constants for toluene with hydroxybutenyl-β-cyclodextrin (HBen-β-CD) and hydroxypropyl-β-cyclodextrin (HP-β-CD).

Solubility isotherms of salicylic acid in an aqueous media in the presence of hydroxybutenyl-β-cyclodextrin (HBen-β-CD) and hydroxypropyl-β-cyclodextrin (HP-β-CD).

Calculation of apparent binding constants for salicylic acid with hydroxybutenyl-β-cyclodextrin (HBen-β-CD) and hydroxypropyl-β-cyclodextrin (HP-β-CD).

Solubility isotherms of citral in an aqueous media in the presence of hydroxybutenyl-β-cyclodextrin (HBen-β-CD) and hydroxypropyl-β-cyclodextrin (HP-β-CD).

Calculation of apparent binding constants for citral with hydroxybutenyl-β-cyclodextrin (HBen-β-CD) and hydroxypropyl-β-cyclodextrin (HP-β-CD).

CYCLODEXTRIN ETHERS

FIELD OF THE INVENTION

This invention relates to a new composition of matter which comprises epoxybutene (EpB) derivatives of cyclodextrins (HBenCD) or mixed ethers of cyclodextrins where at least one of the ether substituents is EpB (HBenRCD where R is an ether substituent other than EpB). This invention also relates to two novel processes for the preparation of cyclodextrin ethers. This invention further relates to inclusion complexes formed between HBenCD or HBenRCD and guest molecules. Such inclusion complexes are useful in pharmaceutical, cosmetic and food applications. Furthermore, this invention relates to the incorporation of HBenCD or HBenRCD or their inclusion complexes in thermoplastic materials, textiles or membranes.

BACKGROUND OF THE INVENTION

Cyclodextrins (CD) are cyclic oligomers of glucose which typically contain 6, 7, or 8 glucose monomers joined by α-1,4 linkages. These oligomers are commonly called α-CD, β-CD, and γ-CD, respectively. Higher oligomers containing up to 12 glucose monomers are known, but their preparation is more difficult.

Those skilled in the art of modifying cyclodextrins will understand that there are a number of ways to indicate the extent to which a cyclodextrin molecule has been modified. Each glucose unit of the cyclodextrin has three hydroxyls available at the 2, 3, and 6 positions. Hence, α-cyclodextrin has 18 hydroxyls or 18 substitution sites available and can have a maximum degree of substitution (DS) of 18. Similarly, β- and γ-cyclodextrin have a maximum DS of 21 and 24, respectively.

It should be noted that at less than full substitution, there will be a distribution of substituted CD molecules in the reaction product. At a low DS, some of the CD molecules potentially will have no substituents. The reported DS will reflect the average value of this distribution.

Topologically, CD can be represented as a toroid in which the primary hydroxyls are located on the smaller circumference, and the secondary hydroxyls are located on the larger circumference. Because of this arrangement, the interior of the torus is hydrophobic while the exterior is sufficiently hydrophilic to allow the CD to be dissolved in water. This difference between the interior and exterior faces allows the CD to act as a host molecule and to form inclusion complexes with guest molecules, provided the guest molecule is of the proper size to fit in the cavity. The CD inclusion complex can then be dissolved in water thereby providing for the introduction of insoluble or sparingly soluble guest molecule into an aqueous environment. This property makes CD particularly useful in the pharmaceutical, cosmetic and food industries. Reviews of CD complexes can be found in *Chem. Rev.*, 1997, 97, 1325–1357 and in *Supramolecular Chemistry*, 1995, 6, 217–223.

The production of CD involves first treating starch with an α-amylase to partially lower the molecular weight of the starch followed by treatment with an enzyme known as cyclodextrin glucosyl transferase which forms the cyclic structure. By conducting the reaction in the presence of selected organic compounds, e.g., toluene, crystalline CD complexes can be formed which facilitate isolation of CD with predetermined ring size. This process has been extensively reviewed by Szejtli et al., *Compr. Supramol. Chem.*, 1996, 3, 41–56. This process yields the native CD discussed above. Table 1 provides a summary of selected physical properties of cyclodextrins.

TABLE 1

Physical Properties of α-, β-, and γ-CD.

| Property | α-CD | β-CD | γ-CD |
|---|---|---|---|
| No. of Glucose Units | 6 | 7 | 8 |
| MW (anhydrous) | 972 | 1135 | 1297 |
| Solubility (water, g/100 ml, 25° C.) | 14.5 | 1.9 | 23.2 |
| Optical Rotation $\alpha_D$ ($H_2O$) | 150.5 | 162.0 | 177.4 |
| Approximate Cavity Diameter (Angstroms) | 5.2 | 6.6 | 8.4 |

As seen in Table 1, there is an unexpected drop in solubility in water for β-CD relative to the α- and γ-CD. This is most unfortunate as β-CD has a highly desirable cavity size and is the most abundant CD available. Many investigators have found that this difficulty can be somewhat overcome by preparing derivatives with low DS (typically lower than 7).

Although many CD derivatives are known, ethers prepared by displacement of halides (U.S. Pat. No. 4,638,058) or by opening of epoxides (U.S. Pat. No. 4,727,064) are preferred. In special cases, the ether may be polyhydroxylated (EP 486445 A2). Preferred methods of ether formation via epoxide opening are disclosed in U.S. Pat. Nos. 3,459,731 and 4,727,064. The preferred epoxides are ethylene oxide (EO) and propylene oxide (PO). It is important to note that opening of the epoxide generates a new primary hydroxyl (from EO) or secondary hydroxyl (from PO). These newly formed hydroxyls can, in turn, react with epoxide, as well, to form oligomeric side chains. Such derivatives are characterized by molar substitution (MS), which is the total number of epoxide groups attached to the cyclodextrin. Because of chain extension, MS can exceed the DS. Other than the hydroxyls formed by opening of the epoxide, these side chains do not contain functionality suitable for further reactions. Investigators have sought to overcome this limitation by incorporation of anionic or cationic groups as part of the starting epoxide (U.S. Pat. No. 3,453,257).

In addition to their utility in the pharmaceutical, cosmetic, and food industries, CD has begun to find utility in the plastic and textile industries. For example, U.S. Pat. No. 5,603,974 discloses a barrier film composition comprised of a thermoplastic and a substituted CD. It was necessary that the CD be substituted in order to obtain sufficient compatibility with the thermoplastic. The invention further required that the substituted CD be "substantially free of an inclusion complex" meaning that a large fraction of the dispersed CD derivative in the film did not contain a guest molecule. This film acts as a barrier to permeants such as water, aliphatic and aromatic hydrocarbons, carboxylic acids, aldehydes, and the like.

Similarly, WO97/30122 discloses a thermoplastic/CD composition for rigid polymer beverage bottles. The preferred thermoplastic is polyethylene terephthalate (PET), and the preferred CD derivatives are acetylated and trimethylsilylated CD. Like U.S. Pat. No. 5,603,974, this invention requires that a guest molecule not be hosted by the CD prior to compounding.

In EP 186,146, the formation of CD complexes with perfumes, insecticides, or fungicides and their incorporation into polyethylene are disclosed. JP 88-265,926 discloses transparent plastics containing slow-release inclusion complexes prepared by mixing polyesters with maltosyl CD complexes of perfumes, insecticides, and the like. The maltosyl CD complexes were reported to give greater transparency than the corresponding complexes prepared from α-, β-, or γ-CD.

JP 01-149,884 discloses sustained-release insecticides, air fresheners, deodorants, etc. in the form of sheet, tape or fiber. Mixing the appropriate CD complex with a plastic material and a water-absorbing polymer forms these sustained-release materials. JP 02-240,166 discloses the preparation and application of complexes of CD and deodorants in the manufacture of plastic products like trash bags.

3,4-Epoxy-1-butene (EpB) is formed by the monoepoxidation of butadiene (U.S. Pat. No. 4,897,498). Ring opening of this epoxide with a lower aliphatic alcohol under acidic conditions leads to the formation of 2-alkoxy-3-butene-1-ols. Under basic conditions, formation of 1-alkoxy-3-butene-2-ols is favored. These butenols can be further reacted with acrylic or methacrylic acids to form acrylic esters, which may be used in subsequent polymerization reactions (U.S. Pat. No. 2,504,082).

Also, the reaction of 3,4-epoxy-1-butene with an oxygen nucleophile in the presence of a Pd(0) complex catalyst leads to the formation of 1,4-dioxy-2-butenes (U.S. Pat. No. 5,189,199). Furthermore, polymerization of 3,4-epoxy-1-butene in the presence of tetrahydrofuran, an acid catalyst, and a nucleophilic initiator provides for the formation of novel polyether compounds (U.S. Pat. No. 5,502,137). All of the products of these reactions are unsaturated, thus providing a functionality useful for further reactions. For example, U.S. Pat. No. 5,502,137 discloses that an unsaturated polyether can be reduced with hydrogen to provide a unique, fully saturated polyether with useful and beneficial properties.

Given the general utility of cyclodextrins in a wide variety of applications, there exists a general need for new CD derivatives that could be utilized in the formation of inclusion complexes. Such inclusion complexes could be preformed for delivery of guest molecules, or the inclusion complexes could be formed as the result of trapping of an unwanted molecule. It would be advantageous if these new CD derivatives could be incorporated into shaped articles. It would be particularly advantageous if the CD derivative contained functionality that would permit further elaboration. We have found that such derivatives can be obtained through the reaction of 3,4-epoxy-1-butene with α-, β-, or γ-CD.

SUMMARY OF THE INVENTION

This invention relates to new compositions of matter, processes for producing new compositions of matter, inclusion complexes comprised of the new compositions of matter and guest molecules, and shaped articles containing inclusion complexes comprised of the new compositions of matter and guest molecules. Specifically, the invention is directed to:

1. A water-soluble host molecule comprised of hydroxybutenyl derivatives of cyclodextrins (HBenCD) or mixed ethers of cyclodextrins where at least one of the ether substituents is hydroxybutenyl (HBenRCD where R is an ether substituent other than hydroxybutenyl) characterized by having DS of about 0.02 to about 9.0 and capable of forming host-guest complexes.

2. An organic solvent miscible host molecule comprised of hydroxybutenyl derivatives of cyclodextrins (HBenCD) or mixed ethers of cyclodextrins where at least one of the ether substituents is hydroxybutenyl (HBenRCD where R is an ether substituent other than hydroxybutenyl) characterized by having DS of about 9.0 to about 18–24 (depending on the type of cyclodextrin utilized) and capable of forming host-guest complexes.

3. Novel processes for the preparation of cyclodextrin ethers.

4. Inclusion complexes comprised of water-soluble HBenCD or HBenRCD and guest molecules wherein HBenCD and HBenRCD (where R is an ether substituent other than hydroxybutenyl) are characterized by having DS of about 0.02 to about 9.0.

5. Inclusion complexes comprised of an organic solvent miscible HBenCD or HBenRCD and guest molecules wherein HBenCD and HBenRCD (where R is an ether substituent other than hydroxybutenyl) are characterized by having DS of about 9.0 to about 18–24 (depending on the cyclodextrin used).

6. Shaped articles containing from about 0.01% to about 10% of one or more inclusion complexes comprised of HBenCD or HBenRCD and guest molecules.

DETAILED DESCRIPTION OF THE INVENTION

One aspect of this invention relates to a new composition of matter comprised of hydroxybutenyl derivatives of cyclodextrins (HBenCD) and mixed ethers of cyclodextrin where at least one of the ether substituents is hydroxybutenyl (HBenRCD where R is an ether substituent other than hydroxybutenyl). These new HBenCD ether derivatives are formed by a base-catalyzed reaction between the CD and 3,4-epoxy-1-butene. Mixed ethers (HBenRCD) can be similarly prepared by reaction with EpB and another etherifying agent, either simultaneously or sequentially.

Figure 1:
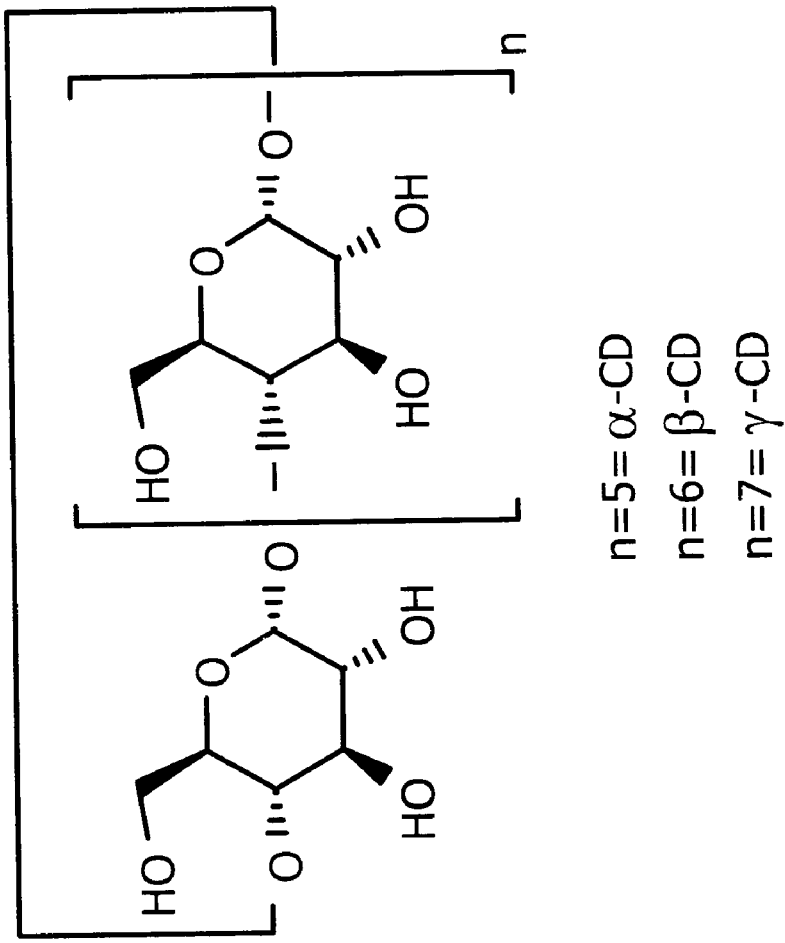
FIG. 1 shows the chemical structure of α-, β-, and γ-cyclodextrins.

Cyclodextrins useful in the present invention include any cyclic oligomers of glucose joined by α-1,4 linkages. The preferred cyclodextrins are those containing 6, 7, or 8 glucose monomers as illustrated in FIG. 1. The most preferred cyclodextrins are those containing 6 or 7 glucose monomers (α-CD or β-CD). Mixtures of α-CD, β-CD, or γ-CD are also useful in the present invention. In the case of mixtures, the amount of α-CD can range from 1–99 weight %, the amount of β-CD can range from 1–99 weight %, and the amount of γ-CD can range from 1–99 weight %. A preferred composition for the mixture is when α-CD is present at 10–90 weight %, β-CD is present at 10–90 weight %, and γ-CD is present at 10–90 weight %.

Figure 2:
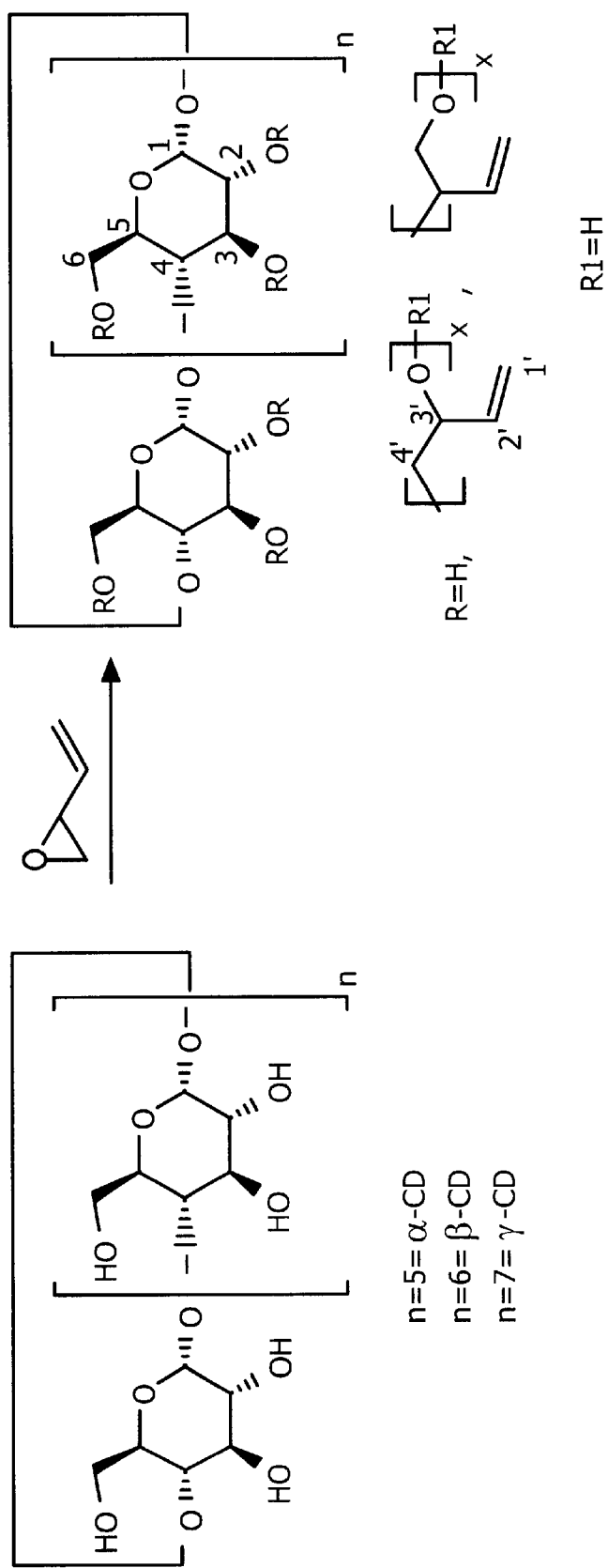
FIG. 2 shows the reaction of cyclodextrins with EpB resulting in either primary or secondary alcohols as products.

The structure of 3,4-epoxy-1-butene and of the product formed in the reaction of CD with EpB is shown in FIG. 2. The average MS (or x) can range from about 0.01 to about 100, where the average MS is the MS divided by the number of anhydroglucose units. The preferred average MS is from about 0.05 to about 10. The most preferred average MS is from about 0.1 to about 7.

As seen from FIG. 2, reaction of the epoxide with the hydroxyl group of the CD can generate a new primary alcohol if the reaction occurs at C3 of EpB or a secondary alcohol if the reaction occurs at C4 of EpB. Prior inventions have indicated that, under basic conditions, reaction with alcohols occurs predominately at C4 and, under acidic conditions, at C3 (U.S. Pat. No. 2,504,082).

In the case of α-CD, the DS can range from about 0.01 to about 18. For β-CD, the DS can range from about 0.01 to about 21; and for γ-CD, the DS can range from about 0.01 to about 24. The preferred DS depends upon the end-use application.

In the case of applications involving enhanced water solubility, which is desirable for pharmaceutical applications, a preferred DS is from about 0.02 to about 9.0. A more preferred DS is from about 1.0 to about 7.0.

If the end-use application requires better solubility in organic solvents or in thermoplastic materials, a higher DS range is preferred. A more preferred DS range in this case is from about 9.0 to about 18–24, depending upon the type of CD (α, β, or γ) utilized. An even more preferred range is from about 12 to about 18–24, depending upon the type of CD utilized.

It will be well understood by those skilled in the art that the most preferred DS and MS requires matching the type of CD, MS, and DS to the exact application. In this context, a broad DS and MS range is contemplated.

As noted earlier, a further aspect of this invention is a composition of matter based upon mixed ethers of cyclodextrin where at least one of the ether substituents is hydroxybutenyl (HBenRCD where R is an ether substituent other than hydroxybutenyl). Epoxides, an O-alkylating agent, that can be used in the preparation of mixed ethers HBenRCD include the lower alkylene oxides such as, for example, ethylene oxide, propylene oxide, butylene oxide, amylene oxide and glycidol. Other epoxides include aryl or halogen substituted alkylene oxides such as styrene oxide or epichlorohydrin. Mixtures of these epoxides can also be utilized in this invention. Preferred lower alkylene epoxides include ethylene oxide and propylene oxide with propylene oxide being the most preferred epoxide. Reaction of these epoxides with CD has many of the same considerations as noted above.

In preparing mixed ethers of CD, it is not necessary that the additional ether groups, R, arise from reaction of CD with an epoxide. The additional ether groups, R, can arise by reaction of CD with non-epoxide O-alkylating agents. Appropriate non-epoxide O-alkylating agents include alkyl-, hydroxyalkyl-, arylalkyl-, carboxyalkyl-, (alkyloxycarbonyl)alkyl-, allyl-, or vinyl-halides, sulfonates or diazomethane. Mixtures of non-epoxide O-alkylating agents can also be utilized. Specific examples of non-epoxide O-alkylating agents include methyl chloride, methyl iodide, methyl bromide, ethyl bromide, propyl bromide, butyl bromide, propyl methyl sulfonate, methyl or ethyl chloroacetic acid, sodium chloroacetate, chloroacetic acid, benzyl bromide, dimethylsulfate, 1-N,N-dialkylamino-2-chloroethane and the like. Preferred non-epoxide O-alkylating agents include methyl chloride, ethyl bromide, and sodium chloroacetate.

In preparing mixed ethers of cyclodextrin where at least one of the ether substituents is hydroxybutenyl, the other substituents can be added to the CD either by a simultaneous addition of EpB and one or more epoxides and/or other O-alkylating agents or by sequential addition of EpB and one or more epoxides and/or other O-alkylating agents. Those skilled in the art will recognize that the order of addition of epoxides/O-alkylating agents can impact substitution patterns and, hence, physical properties.

All of the known processes for preparing CD ethers involve the reaction of CD with O-alkylating agents under basic conditions. In particular, two processes are practiced. Although both of these processes can be used to prepare the HBenCD and HBenRCD compounds of the present invention, these processes have proven to be inferior to the processes of the present invention.

In the first known process, which we term the "aqueous process," the CD is dissolved in water, an alkali metal hydroxide (typically NaOH or KOH) is added, and the O-alkylating agent is then added to the solution. An organic co-solvent can also optionally be utilized in this process. The reaction is brought to a contact temperature of 0–140° C. The reaction is typically conducted at atmospheric pressure, although the reaction can be performed in pressurized vessels.

The aqueous process has some advantages as well as disadvantages. One of the advantages of the aqueous process is the enhanced ability to control DS, MS and substitution patterns. The disadvantages of this process include (1) the potential high concentration of inorganic salts used which must be removed from the reaction mixture, (2) the reaction of O-alkylating agents with water rather than CD, (3) the formation of polyether glycols due to initiation of ring opening of epoxides with water, and (4) the isolation of the product from water.

Such a process can nonetheless be utilized in making the novel compositions described in this invention. For example, if the reaction between CD and EpB is carried out in an aqueous alkali solution optionally containing an organic co-solvent, regioselectivity can be obtained by control of the temperature (0–140° C.) and the concentration of base. At low temperatures and low concentration of base, reaction at C2 is favored over that at C6. At low temperatures and high concentration of base, reaction at C6 is favored over reaction at C2. This process is described in WO 90/12035, EP 0536318 B1, U.S. Pat. Nos. 4,870,060, 4,764,604 and 5,173,481; the entire contents of which are hereby incorporated by reference. It is important to note that none of these references discloses hydroxybutenyl derivatives of cyclodextrin or mixed ethers of cyclodextrins in which one of the substituents is hydroxybutenyl.

We have surprisingly and unexpectedly found that when the reaction of cyclodextrin with epoxybutene is carried out at elevated temperature and pressure, and by introducing epoxybutene into the reaction mixture after the reaction mixture has been heated to reaction temperature, several advantages are seen. First, the reaction is over quickly. U.S. Pat. No. 3459731 and 5173481 teach that reaction times for the reaction of cyclodextrins with propylene oxide (a more reactive epoxide than EpB) are lengthy, generally more than 18 hours. By using our procedure, reaction times are reduced to less than 2 hours and completion of the reaction chemistry can be determined by monitoring the pressure drop on the reaction vessel. Furthermore, an organic co-solvent is not necessary.

Second and more importantly, the reaction chemistry is much more consistent and fewer by-products resulting from the reaction of epoxybutene with water and other epoxybutene molecules. As a direct comparison of the impurities produced from the reaction of EpB with β-cyclodextrin, we carried out two experiments. In the first, EpB was added before the reaction mixture was heated to reaction temperature, and in the second, EpB was added after the reaction mixture was heated to the reaction temperature. The amount of butene diol was quantified in each reaction mixture. Butene diol in the former reaction was 6.0 weight % of the solution, while in the latter butene diol was found to be only 3.9 weight % of the solution. The level of EpB oligomers was also low at 0.5 weight % versus 0.74 weight %, respectively. The DS of the product obtained in both cases was similar.

Since these by-products are water soluble like. the product, they can be difficult to remove from the product and purification becomes troublesome. The product produced from this procedure, on the other hand, which contains fewer by-products, requires less purification and is more easily isolated in higher yields. By-products that are produced can be removed by liquid-liquid extraction of the aqueous solution of HBenCD or HBenRCD with a water immiscible organic solvent. Suitable organic extraction solvents may include hydrocarbons (such as heptane or hexane), aromatics (such as benzene, toluene or xylene), ketones (such as methyl ethyl ketone or methyl isobutyl ketone), chlorinated solvents such as (chloroform or methylene chloride) or esters (such as ethyl acetate, propyl acetate and the like). The preferred solvents for this extraction are esters and the most preferred solvent is ethyl acetate.

Accordingly, the first process for the preparation of cyclodextrin ethers according to the present invention involves heating a reaction mixture comprising a cyclodextrin, water, and an alkaline metal hydroxide to an elevated temperature; and introducing an O-alkylating agent into the reaction mixture at the elevated. temperature to form a cyclodextrin ether. Preferably, the elevated temperature ranges from about 50 to about 200° C., and more preferably, from about 100 to about 140° C. Preferably, the reaction pressure ranges from 0.1 to 10 atmospheres, and more preferably from 1.0 to 5 atmospheres. By "alkaline metal hydroxide," we mean an alkali or an alkaline earth metal hydroxide. Potassium hydroxide is a preferred alkaline metal hydroxide for use in this process. The range of alkaline metal hydroxide stoichiometry can be from 0.1 to 20 molar equivalents, with 0.1 to 10 molar equivalents being preferred, and 0.1 to 1 molar equivalents being especially preferred. The preferred O-alkylating agent is EpB.

Those skilled in the art will realize that the DS of the product will be highly dependent on the stoichiometry of EpB employed. To prepare low DS HBenCD, the amount of EpB employed may range from 0.1 to 20 equivalents of EpB per cyclodextrin molecule, preferably 0.1 to 10 equivalents of EpB per cyclodextrin molecule, and most preferably 5–8 equivalents of EpB per cyclodextrin molecule.

The product distribution obtained from the reaction of EpB with cyclodextrin under these conditions provides a CD having a DS range from DS about 2–11 and centered on ca. DS 6. These CD ethers have excellent water solubility (see Table 4). It is difficult to separate the HBenCD from the water-soluble by-products that were also present in the reaction mixture. The most effective method found to remove these by-products was to extract them into an organic solvent and then separate the aqueous and organic media. Due to the high solubility of the product in water, only small amounts of product were lost to the organic layer; hence, the isolated yield of product was excellent. Those skilled in the art of purification of organic compounds will realize that the purity of the isolated product will depend on the volume of organic solvent employed relative to the amount of aqueous material present, the number of extractions performed, and the temperature at which the extractions are performed.

The amount of solvent employed can vary from 10% to 500% of the volume of the aqueous phase present and the number of extractions performed can vary from one to ten. The temperature at which the extraction is carried out can vary from 10° C. to just below the boiling point of the solvent. The most preferred amount of solvent was a 1:1 volume ratio with the reaction mixture, the preferred number of extractions was six, and the most preferred extraction temperature was 70° C.

Figure 3:
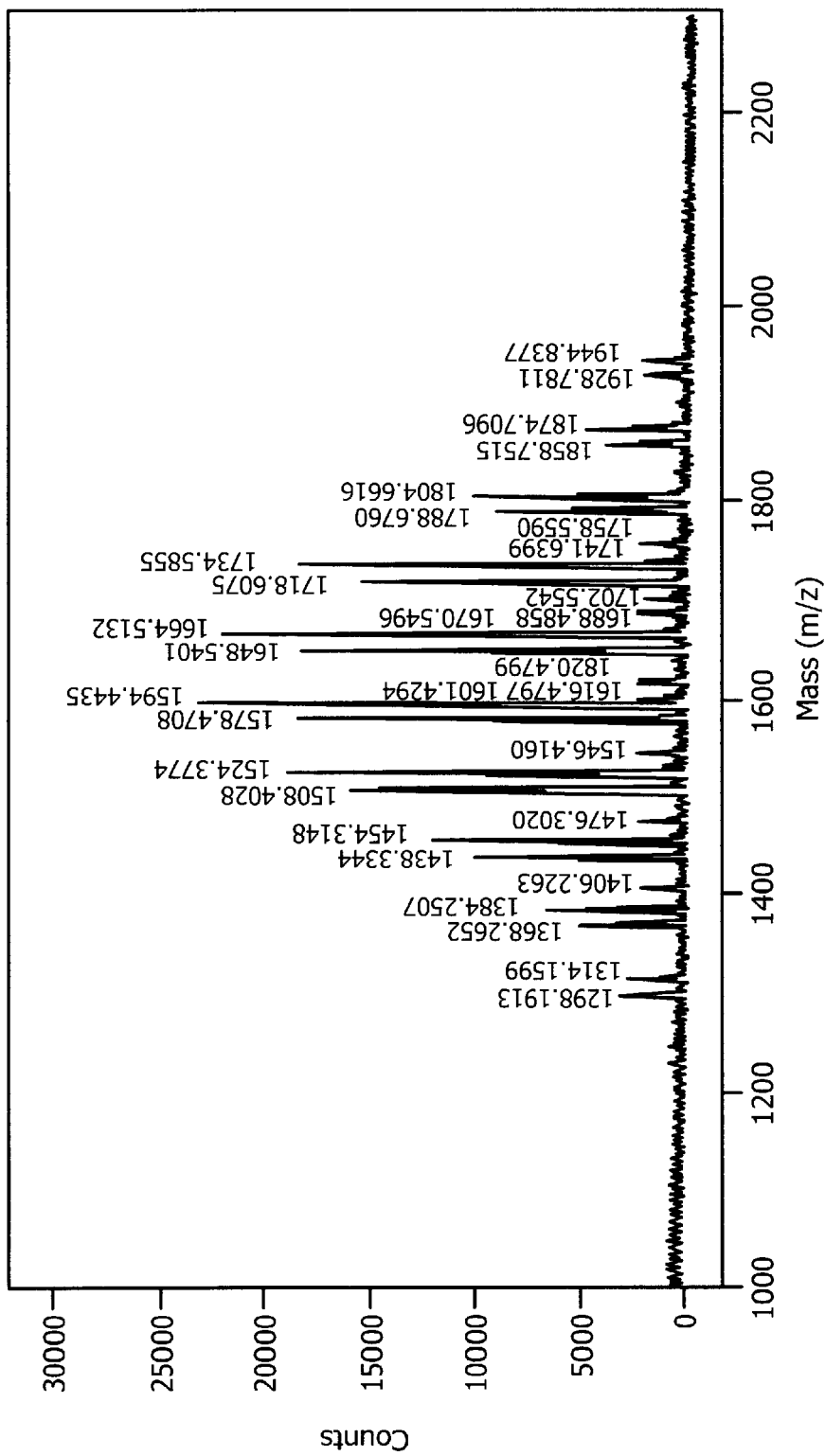
FIG. 3 is a MALDI-TOF spectrum of an HBen-β-CD in which the MS ranges from 2–11 and is centered at MS 6.4.

After the by-products were removed by extraction with an organic solvent, the product was isolated from the aqueous phase by co-evaporating the water with an organic solvent. Suitable solvents for this purpose include any number of organic solvents which form low-boiling azeotropes with water including alcohols, esters, aromatics and ketones. The preferred solvents are alcohols and the most preferred solvent is ethanol. The product was isolated as viscous oil, which solidified leaving a white powder. MALDI-TOF mass spectrometry indicated that the product was actually a mixture of a number of compounds with differing levels of substitution about the cyclodextrin ring (see FIG. 3).

The process developed for the preparation of low DS cyclodextrins will not provide material with a DS greater than 10.5–11. When attempts were made to prepare hydroxybutenylated-β-cyclodextrin derivatives with higher degrees of substitution (target DS 14), we were frustrated to find that the product obtained from the reaction was almost invariably more lowly substituted than desired. Increasing the temperature at which the reaction was run, increasing the reaction time, the equivalents of the alkaline metal base, the equivalents of EpB used, or any combination thereof, did not result in the desired level of substitution. These attempts instead resulted in material with a degree of substitution no greater than 10.5–11.

However, we have surprisingly found that the addition of equivalent amount of an organic co-solvent to the aqueous media and an increase in the equivalents of the alkaline metal base from 0.25 equivalents to 1.0 equivalents resulted in products with higher levels of substitution (see Example 4). Suitable solvents that can be used include water miscible organic solvents such as alcohols, ketones and esters. The preferred solvents are alcohols and the most preferred solvent is isopropanol.

Figure 4:
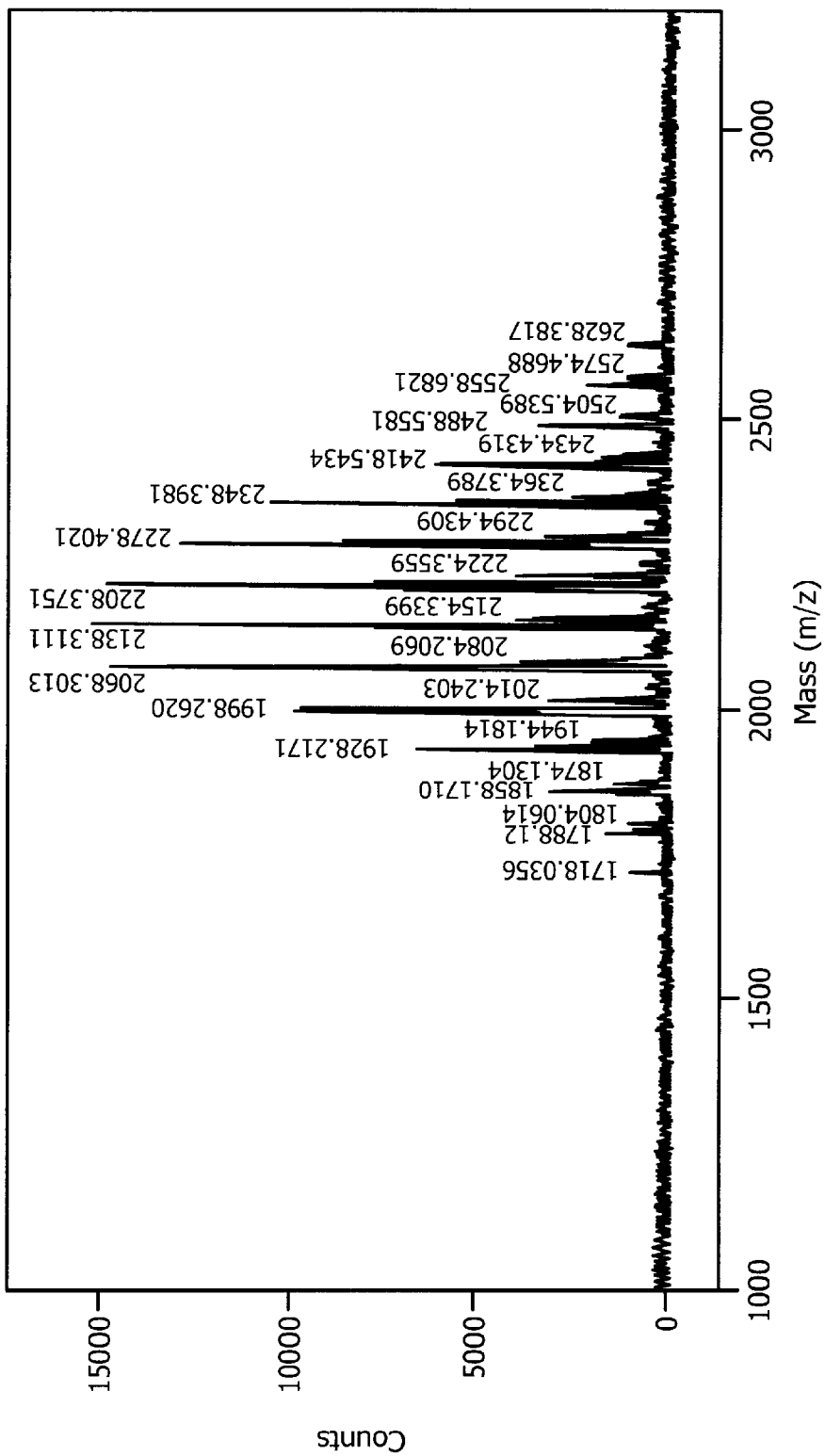
FIG. 4 is a MALDI-TOF spectrum of an HBen-β-CD in which the MS ranges from 8–21 and is centered at MS 13.5.

Analysis of the reaction mixture by MALDI-TOF mass spectrometry indicated the presence of DS 14.5 material (with DS ranging from 8 to 21). Isolation of the product found it to be of slightly lower DS (13.5) (see FIG. 4), probably due to loss of some of the more highly substituted materials during isolation resulting in a slightly lower DS in the final product.

Hydroxybutenylated-β-cyclodextrin with higher levels of substitution are difficult to purify using the extraction method employed in the purification of the lower substituted products. Their greater solubility in organic media caused them to be extracted in the organic phase along with the byproducts of the reaction resulting in significant yield losses. As a result, this derivative was purified by dialysis. Dialysis is a known method for the purification of derivatized cyclodextrins (U.S. Pat. No. 5,173,481; the entire content of which is hereby incorporated by reference).

The second known process for preparing cyclodextrin ethers is the "non-aqueous process." In the non-aqueous process, the CD is suspended in a reaction medium containing the O-alkylating agent(s), and the reaction is carried out at a suitable temperature.

Like the aqueous process, the non-aqueous process has certain advantages as well as disadvantages. The advantage of this process is the ability to obtain higher DS and MS via reaction at each of the three hydroxyls of the CD, regardless of the type of catalyst or solvent used. The disadvantages of this process include (1) the high concentration of inorganic salts which must be removed from the reaction mixture, (2) the reaction of O-alkylating agents with alcohol rather than CD, (3) the formation of polyether glycols due to initiation of ring opening of epoxides with alcohol, and (4) the lack of ability to control DS, MS and substitution patterns.

Such a process can nonetheless be utilized in making the novel compositions described in this invention. This type of process is disclosed in U.S. Pat. No. 3,459,731; the entire content of which is hereby incorporated by reference. Although butadiene oxide was listed as a possible epoxide that could be used in reactions with CD in U.S. Pat. No. 3,459,731, butadiene oxide was not specifically claimed as an etherfying agent of CD, and insufficient detail was provided that would enable one of ordinary skill in the art to reproduce their invention to prepare water soluble, low DS cyclodextrin derivatives. Furthermore, the invention of U.S. Pat. No. 3,459,731 is directed towards the preparation of CD ether derivatives having a very high DS and MS for use in the preparation of polyurethane foams. The inventors did not contemplate or anticipate utilizing the CD ether as host molecules in the formation of inclusion complexes nor that these ethers would have solubility in water or in thermoplastic resins. Indeed, practice of U.S. Pat. No. 3,459,731 would not provide a CD ether that is soluble in water or thermoplastics and that is suitable for complex formation.

We have surprisingly and unexpectedly found that the reaction of an alkaline salt of CD with EpB, epoxide or other alkylating agents in a non-aqueous environment provides for many significant advantages over the non-aqueous processes previously described in the art. The advantages of the process of the present invention over those previously known in the art include (1) the elimination of excess inorganic salts and resulting need for extensive purification, (2) the minimization of side reactions which lead to the formation of polyether glycols, and (3) the elimination of water from the reaction mixture. The alkaline CD salt is formed by first dissolving the CD in an aqueous solution containing an alkali or alkaline earth (collectively "alkaline") metal hydroxide, followed by isolation by crystallization of the CD alkaline salt from a suitable solvent, washing to remove excess alkaline metal hydroxide, and drying to remove the crystallization solvent.

Preferred alkaline metal hydroxides include NaOH, KOH, LiOH and $Ca(OH)_2$. The most preferred alkaline metal hydroxides are KOH and NaOH. The concentration of alkaline metal hydroxide used for dissolving the CD can range from 1–75 weight %. The most preferred concentration of alkaline metal hydroxide is from 30–50 weight %.

Preferred crystallization solvents include methanol, ethanol, n-propyl alcohol, iso-propyl alcohol, n-butyl alcohol and tert-butyl alcohol. The solvents can optionally contain 1–30% $H_2O$. The most preferred crystallization solvent is ethanol.

The CD alkaline salt is then suspended in an organic solvent containing the desired amount of EpB or EpB/O-alkylating agent(s). The reaction is preferably conducted at elevated temperature and, if necessary, pressure. The preferred temperature range is from about 50° C. to about 250° C. The more preferred temperature range is from about 80° C. to about 150° C. The preferred pressure range is from about atmospheric pressure to about 200 psi. The more preferred pressure range is from about 10 psi to about 100 psi.

Preferred organic solvents include n-propyl alcohol, iso-propyl alcohol, n-butyl alcohol, and tert-butyl alcohol. The most preferred organic solvents are isopropyl alcohol and tert-butyl alcohol. The amount of EpB or EpB/O-alkylating agent(s) added to the reaction mixture depends upon the desired DS and MS. In this context, a wide range of EpB or EpB/O-alkylating agent(s) is contemplated.

After sufficient contact time at the desired temperature and pressure, the reaction mixture is cooled and filtered to remove any solids. The inert organic solvent is removed under reduced pressure to provide the desired product. The product can then be further purified by means known to those skilled in the art.

Another aspect of this invention relates to inclusion complexes comprised of HBenCD or HBenRCD and guest molecules. These inclusion complexes can be separated into two broad classes depending upon their utility. This aspect of the invention is based on the surprising and unexpected observation that HBenCD and HBenRCD derivatives exhibit very high solubility in water (DS from about 0.02 to about 9.0) and thermoplastics (DS from about 9 to about 18–24 depending upon the CD employed). Furthermore, we have found that HBenCD and HBenRCD derivatives can form inclusion complexes with a wide variety of guest molecules. The apparent binding constant for many of the guest molecules are higher than those observed with other CD derivatives. These HBenCD and HBenRCD/guest molecule complexes are very soluble in water.

The first class is intended for use in the pharmaceutical, cosmetic, food, and related industries and their utility comes from the fact that these inclusion complexes can exhibit enhanced water solubility relative to the parent hydrophobic guest, thereby providing a means for introduction of insoluble or sparingly soluble guest molecules into an aqueous environment. Furthermore, complexation of the guest molecule can stabilize and decrease the volatility of drug molecules. In general, the HBenCD or HBenRCD derivatives used for this class of inclusion complexes have a preferred DS from about 0.02 to about 9.0.

Examples of guest molecules include anti-viral agents, anti-cancer agents, agents for treatment of neural disorders, anti-microbial and anti-fungal agents, steroids, non-steroid anti-rheumatic agents, cardiac glycosides, oligionucleotides, and derivatives of benzodiazepine, benzimidazole, piperidine, piperazine, imidazole, or triazole. Particularly useful guest molecules for forming the inclusion complexes of this invention include AZT, prostaglandin, ibuprofen, hydrocortisone, sodium loxoprofen, testosterone, piroxicam, benexate, iodine, dexamethasone, nitroglycerin, cefotiam hexetil HCl, thyaprofenic, chlordiazepoxide, itraconazole, garlic oil, and topiramate. In pharmaceutical applications, such complexes can be utilized in oral formulations, ophthalmic preparations, nasal drug delivery, dermal formulations, or rectal formulations.

The second class of inclusion complexes is intended for use in thermoplastic shaped articles. This application requires solubility of the CD ether in thermoplastic materials, and hence, a higher DS range is preferred. A preferred DS range in this case is from about 9.0 to about 18–24, depending upon the type of CD utilized. A more preferred CD range is from about 12 to about 18–24, depending upon the type of CD utilized. The shaped articles preferably contain from about 0.01 weight % to about 10 weight % of these inclusion complexes, and more preferably from about 1 weight % to about 5 weight % of inclusion complex.

Examples of guest molecules for this application include fragrances, flavors, fungicides, antimicrobial agents, amines, dianines, deodorants, insecticides, and the like. Of particular value in the invention are fragrances, flavors and fungicides. Examples of fragrances and flavors include, but are not limited to, oils of sandalwood, lemon, Douglas fir, patchouli, strawberry, and vanilla. Examples of fungicides include, but are not limited to, copper salts, zinc salts, sodium bisulfite, EDTA, formaldehyde and isothiazolin. Combinations of isothiazolin with copper, zinc, or EDTA are particularly useful in this invention.

Thermoplastic materials suitable for compounding with the CD inclusion complexes include, but are not limited to, polyolefins, aromatic polyesters, vinyl polymers, acrylic polymers, polynitriles, polyamides, aliphatic polyesters, aromatic-aliphatic copolyesters, $C_1$–$C_{10}$ esters of cellulose, polystyrene, polycarbonate, polylactates, polyhydroxybutyrates, polyhydroxybutyrate-valerate copolymers, polycaprolactone, cellophane and mixtures thereof. Preferred thermoplastic materials include polyethylene, polypropylene, polyethylene-propylene copolymers, polyethylene terephthalate, polyethylene naphthalate, polyethylene terephthalate-naphthalate copolymers where the mole % of terephthalate dicarboxylate can vary from 1–99 mole %, polytetramethylene adipate-terephthalate copolymers where the mole % of aromatic dicarboxylate can vary from 10–60 mole %, cellulose acetate, cellulose acetate propionate, cellulose acetate phthalate, cellulose acetate butyrate, cellulose propionate, cellulose butyrate, polylactic acid, polyvinyl chloride, polystyrene, polyethylene-vinyl acetate copolymers, polyethylene-vinyl alcohol copolymers and mixtures thereof.

The inclusion complexes according to the present invention may be formed by any manner known in the art. Such complexes may be formed, for example, by the techniques described in *Chem. Rev.*, 1997, 97, 1325–1357 and in *Supramolecular Chemistry*, 1995, 6, 217–223; the contents of which are hereby incorporated by reference.

This invention can be further illustrated by the following examples of preferred embodiments thereof, although it will be understood that these examples are included merely for purposes of illustration and are not intended to limit the scope of the invention unless otherwise specifically indicated. The starting materials are commercially available unless otherwise described. All percentages are by weight unless otherwise described.

EXAMPLES

Hydroxybutenylcyclodextrins were assayed using high pressure liquid chromatography (HPLC). A Hewlett Packard 1100 Liquid Chromatograph with an integrated pump, autosampler, and diode array detector was utilized. A Sedex Model 55 Evaporative Light Scattering Detector was connected in series with the diode array detector. The diode array detector (UV at 210 nm, 16 nm bandwith, 8 nm slit) was used for the determination of the key impurities, while the light scattering detector was used for the determination of the HBenCD. A Shodex Asahipak GS-220 HQ analytical column (300×7.6 mm, 6$\mu$) with a Shodex Asahipak GS-2G 7B guard column (50×7.6 mm) was employed. The sample injection size was 20 $\mu$L and the mobile phase was 35/65 acetonitrile/water at a flow rate of 0.6 mL/min. Standards and samples were prepared in 50/50 acetonitrile/water.

Determination of the MS and the MS range of the products were determined by MALDI-TOF Mass Spectrometry (PerSeptive Biosystems Voyager Elite DE MALDI/Time-of-Flight Instrument). The MS was determined by a weighted average of the components in the sample. Salt content of the samples was determined using a Philips PW2400 x-ray fluorescence spectrometer with a Cr target tube. The data was analyzed using a Omega Data Systems UniQuant package.

Example 1

Preparation of the Alkali Metal Salt of β-Cyclodextrin

The salt of β-cyclodextrin (β-CD) was prepared by dissolving 3.0 moles of β-CD in 12 L of demineralized water and adding 66 moles of NaOH or KOH pellets. The sodium (or potassium) salt of β-CD was isolated by slowly adding the solution to 20 L of stirred anhydrous ethanol at room temperature which resulted in the precipitation of the product. The slurry was stirred overnight to allow for crystallization of the product. The product was isolated by filtration and the filter cake washed with anhydrous ethanol. Upon drying, 2.7 moles of product were obtained.

Example 2

Preparation of the High MS Hydroxybutenyl-β-Cyclodextrin (HBen-β-CD) in Organic Solvent.

A 1-liter glass-lined pressure reactor was charged with the potassium salt of β-CD (0.75 mol) and 254 g of t-BuOH. EpB (1.7 mol) was charged to the reaction vessel and the vessel was sealed. The reaction mixture was heated to 113–120° C., and the pressure in the vessel rose to 3.4 bar. The reaction mixture was stirred at 113–120° C. for 7 hours. The reaction mixture was allowed to cool to room temperature, the pressure was lowered to atmospheric pressure and the sample was discharged from the vessel. The reaction mixture was transferred to a filter funnel and solids were removed by filtration. The solids were washed with t-BuOH and the filtrate combined with the mother liquor. The combined solution was concentrated in vacuo at 80° C. to yield 63 g of an amber oil. MALDI-TOF mass spectrometry confirmed the presence of EpB/β-cyclodextrin adduct with a MS range centered on MS 19.

EXAMPLE 3

Preparation of Low MS Hydroxybutenyl-β-Cyclodextrin (HBen-β-CD) at Elevated Temperature and Pressure.

Water (400 ml), β-cyclodextrin (280 g, 0.25 moles) and KOH (3.46 g, 0.062 moles) were charged to a pressure reactor and heated to 100° C. with stirring. 3,4-Epoxy-1-butene (EpB) (140.2 g, 2.0 moles) was charged to the reaction vessel over a period of 35–45 minutes increasing the reactor pressure in the reaction vessel by 1.5 bar. EpB was quickly consumed as evidenced by the vapor pressure decreasing to pre-addition levels within 15 minutes. The reaction mixture was held at 100° C. for an additional 1 hour to ensure complete reaction. The reaction mixture was allowed to cool to below 50° C. and was neutralized with HCl. Extraction of the aqueous layer with ethyl acetate removed reaction by-products. Co-evaporating the water with ethanol provided the product as off-white crystals in 80–85% yield. The final product was dried in a vacuum oven at prior to characterization by MALDI-TOF mass spectrometry, HPLC and elemental analysis. Following this general procedure, six samples were prepared and their analyses are summarized in Table 2.

TABLE 2

Summary of Analyses of HBen-β-CD

| Sample | Wt. % Assay[1] | Wt. % Butenediol[1] | MS[2] | MS Range[2] | Wt. % KCl[3] | M.P. (° C.) |
|---|---|---|---|---|---|---|
| 1 | 95.4 | 3.9 | 6.02 | 2–10 | 1.10 | 175–200 |
| 2 | 94.2 | 3.2 | 6.28 | 2–10 | 0.97 | 178–204 |
| 3 | 95.6 | 2.9 | 6.37 | 1–11 | 0.98 | 165–185 |
| 4 | 94.15 | 2.8 | 6.47 | 2–10 | 1.05 | 179–206 |
| 5 | 94.8 | 2.7 | 5.72 | 2–10 | 1.05 | 168–205 |
| 6 | 102.5 | 3.1 | 6.6 | 2–11 | 1.08 | 171–208 |

[1]By HPLC.
[2]By MALDI-TOF Mass Spectrometry using acetonitrile-water as the matrix solvent.
[3]By Elemental Analysis.

Example 4

Preparation of High MS HBen-β-CD in a Water/Organic Solvent System

Water (200 mL), isopropyl alcohol (200 mL), β-cyclodextrin (252 g, 0.22 moles) and KOH (12.54 g, 0.22 moles, 1 eq.) were charged to a pressure reactor and heated to with stirring. 3,4-Epoxy-1-butene (EpB) (350 mL, 311.5 g, 4.44 mol) was charged action vessel over a period of 35–45 minutes resulting in an increase in the reactor pressure by 3.0 bar. EpB was consumed quickly with the vapor pressure decreasing to pre-addition levels within 1 hour. The reaction mixture was held at 100° C. for an additional 2 hours to ensure complete reaction. The reaction mixture was allowed to cool to below 50° C. was neutralized with HCl. A portion of reaction mixture was purified by dialysis. After solvent removal the product was obtained as an off-white powder. The MALDI-TOF spectrum of the material confirmed the product to have a MS of 13.5.

Example 5

Preparation of Hydroxybutenyl-α-Cyclodextrin (HBen-α-CD)

Water (400 mL), α-cyclodextrin (280 g, 0.29 moles) and KOH (4.10 g, 0.25 moles) were charged to a pressure reactor and heated to 100° C. with stirring. 3,4-Epoxy-1-butene (EpB) (162.6 g, 2.32 moles) was pumped into the reaction vessel over a period of 35–45 minutes, increasing the reactor pressure by approximately 1.5 bar. EpB was quickly consumed with the reactor pressure falling to pre-addition levels within 15 minutes. The reaction mixture was held at 100° C. for 1 hour to ensure complete reaction. The heat source was removed and the reaction mixture was allowed to cool to below 50° C. The reaction mixture was neutralized with HCl. This solution was extracted with ethyl acetate at 70° C. to remove by-products of the reaction. Co-evaporating the solvent with ethanol provided the product as off-white crystals in 80–85% yield. Once isolated, the final product was dried in a vacuum oven at 50° C. for 72 hours prior to characterization by MALDI-TOF mass spectrometry, by HPLC and by elemental analysis. Following this general procedure, four samples were prepared and their analyses are summarized in Table 3.

TABLE 3

Analyses of the Samples of HBen-α-CD.

| Sample | Wt. % Assay[1] | Wt. % Butene-diol[1] | MS[2] | MS Range[2] | Wt. % KCl[3] | M.P. (° C.) |
|---|---|---|---|---|---|---|
| 1 | 101.5 | 4.0 | 6.01 | 2–10 | 1.06 | 160–180 |
| 2 | 98.3 | 2.7 | 5.61 | 2–10 | 1.38 | 160–200 |
| 3 | 95.8 | 3.2 | 5.05 | 1–10 | 0.62 | 158–182 |
| 4 | 98.3 | 3.4 | 5.41 | 1–10 | 1.15 | 158–177 |

[1]By HPLC.
[2]By MALDI-TOF Mass Spectrometry using acetonitrile-water as the matrix solvent.
[3]By Elemental Analysis.

Example 6

Solubility Assay for HBen-β-CD

The solubility of the hydroxybutenyl-β-cyclodextrins (HBen-β-CD) in selected solvents was determined by the addition of 150 μL portion of the studied solvent into a test tube which contained 300 mg of HBen-β-CD. The sample was sonicated for 10 minutes at 25° C. Additional 150 μL portions of solvent were added until complete dissolution of the solid was observed.

Table 4 details the solubility of MS 6.0 and 6.5 hydroxybutenyl-β-cyclodextrin (HBen-β-CD) in water, ethanol-water mixtures, and propylene glycol. The material shows excellent solubility in all three solvent systems. Only a slight difference in solubility is seen between the MS 6.0 and MS 6.5 materials and only in one solvent (96% ethanol). Furthermore, the product exhibited greatly improved solubility in water compared to the parent cyclodextrin (cf. Table 1).

TABLE 4

Solubility of Hydroxybutenyl-β-Cyclodextrin (HBen-β-CD) in Various Solvents.

| Solvent | Solubility of MS 6.0 HBen-β-CD | Observation | Solubility of MS 6.5 HBen-β-CD | Observation |
|---|---|---|---|---|
| Water | ≧50% | Wettable; viscous, pale yellow solution | ≧50% | Wettable; viscous, pale yellow solution |
| 15% EtOH | ≧50% | Wettable; viscous, pale yellow solution | ≧50% | Wettable; viscous, pale yellow solution |
| 30% EtOH | ≧50% | Very well wetted; viscous, pale yellow solution | ≧50% | Very well wetted; viscous, pale yellow solution |
| 60% EtOH | ≧50% | Very well wetted; viscous, pale yellow solution | ≧50% | Very well wetted; viscous, pale yellow solution |
| 96% EtOH | ≧40% | Very well wetted; viscous, pale | ≧50% | Very well wetted; viscous, pale yellow |
| Propylene glycol | ≧40% | Very well wetted; viscous, pale yellow solution | ≧40% | Very well wetted; viscous, pale yellow solution |

Example 7

Solubility Assay for HBen-β-CD

The solubility isotherms of hydroxybutenyl-β-cyclodextrin (HBen-β-CD) and hydroxypropyl-β-cyclodextrins (HP-β-CD) were determined by adding excess amounts of guest molecules to 5.0 cm$^3$ solutions of HBen-β-CD and HP-β-CD at 0%, 0.5%, 1.0%, 5.0%, 10.0% and 20% concentrations. The suspensions were stirred for 24 hours at 25° C. The undissolved residues were removed by filtration through a 0.22 µM filter. The solutions were diluted with a 1:1 water/ethanol mixture and concentrations of the guest molecules were determined spectrophotometrically using an HP 8542 diode array spectrophotometer. The solubility of the guest molecules was represented as a function of the CD derivative concentration. The apparent binding constants were calculated from the slope of the solubility isotherm. The guest molecules evaluated were water-immiscible pharmaceuticals, fragrances, and other organic molecules. These include hydrocortisone, ibuprofen, glibenclamide, toluene, salicylic acid and citral (the main flavoring component of lemon oil, a mixture of cis- and trans-citral).

Graphs of the solubility of these materials versus varying concentrations of HBen-β-CD or HP-β-CD are shown in FIGS. 5, 7, 9, 11, 13 and 15. The data depicted in these figures indicate that, with the exception of hydrocortisone, 14Ben-β-CD is more effective in solubilizing these guest molecules than hydroxypropyl-β-CD, the current commerical cyclodextrin derivative of choice in the solubilization of water-immiscible materials.

Figure 5:
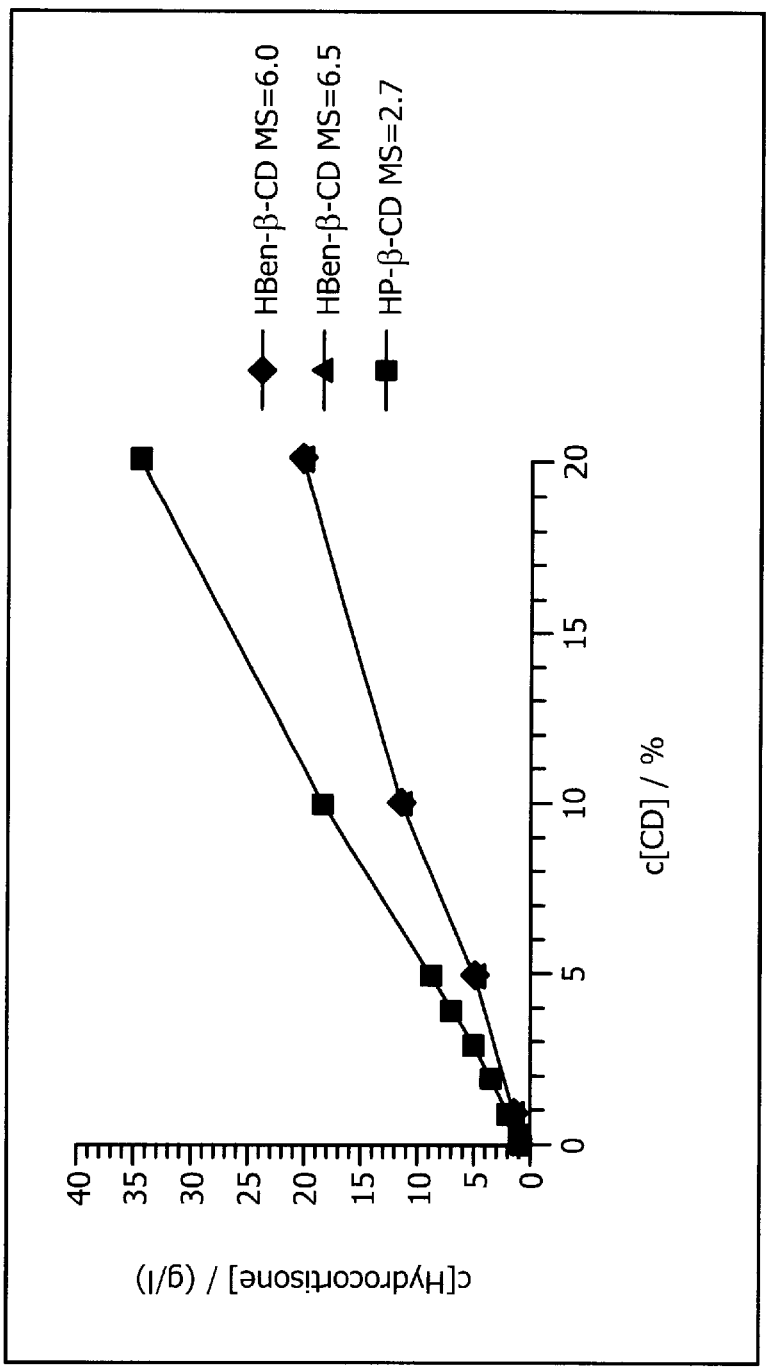
FIG. 5 shows the solubilty isotherms of hydrocortisone in an aqueous media in the presence of MS 6.0 and 6.5 hydroxybutenyl-β-cyclodextrin (HBen-β-CD) and hydroxypropyl-β-cyclodextrin (HP-β-CD).
Figure 6:
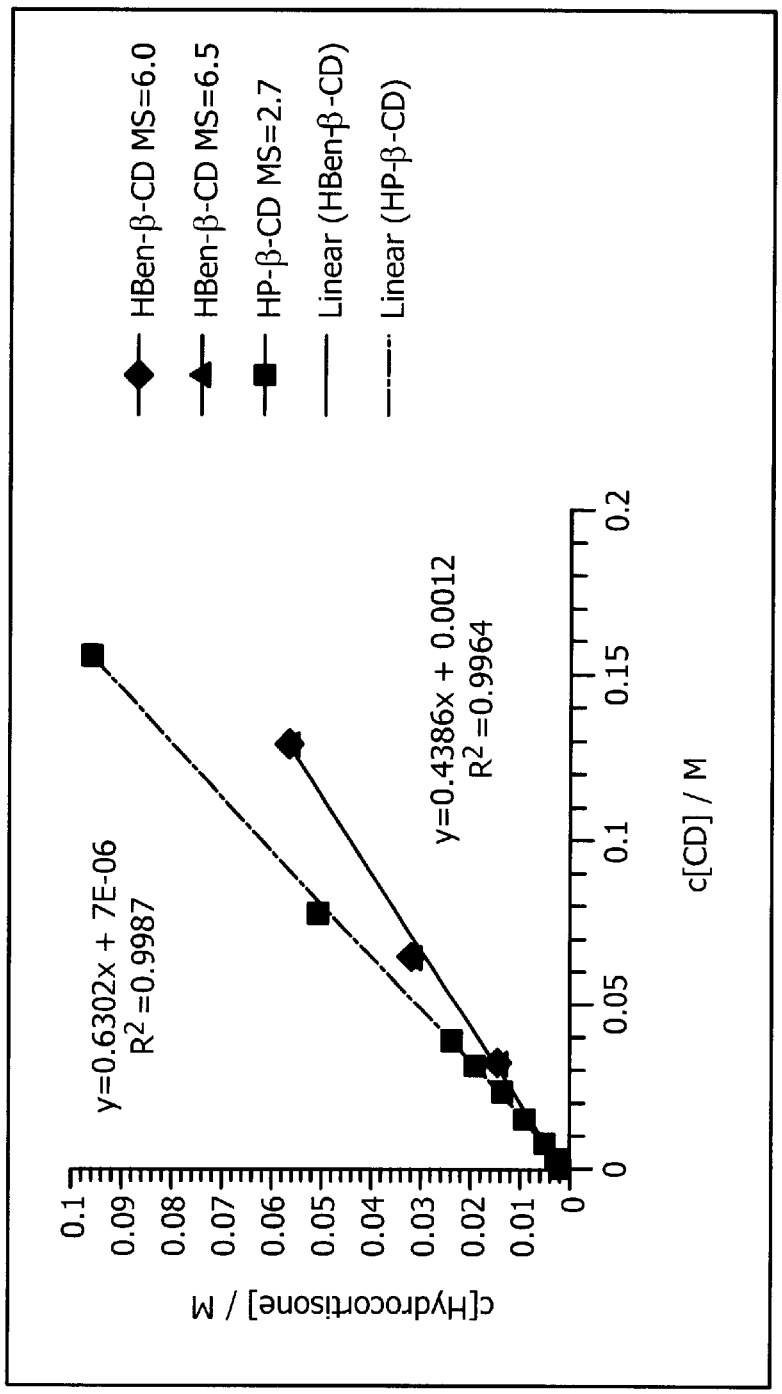
FIG. 6 shows the calculation of apparent binding constants for hydrocortisone with MS 6.0 and 6.5 hydroxybutenyl-β-cyclodextrin (HBen-β-CD) and hydroxypropyl-β-cyclodextrin (HP-β-CD).
Figure 7:
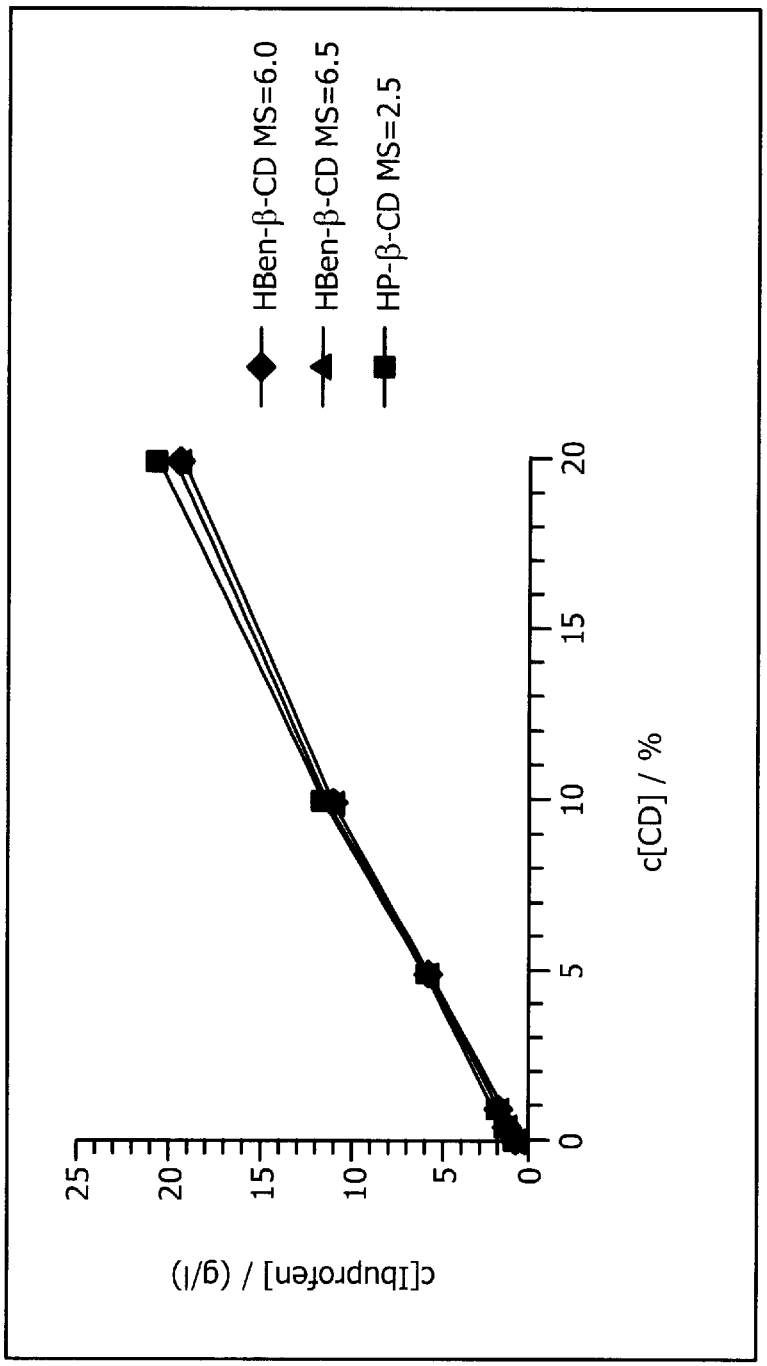
FIG. 7 shows the solubilty isotherms of ibuprofen in an aqueous media in the presence of MS 6.0 and 6.5 hydroxybutenyl-β-cyclodextrin (HBen-β-CD) and hydroxypropyl-β-cyclodextrin (HP-β-CD).
Figure 8:
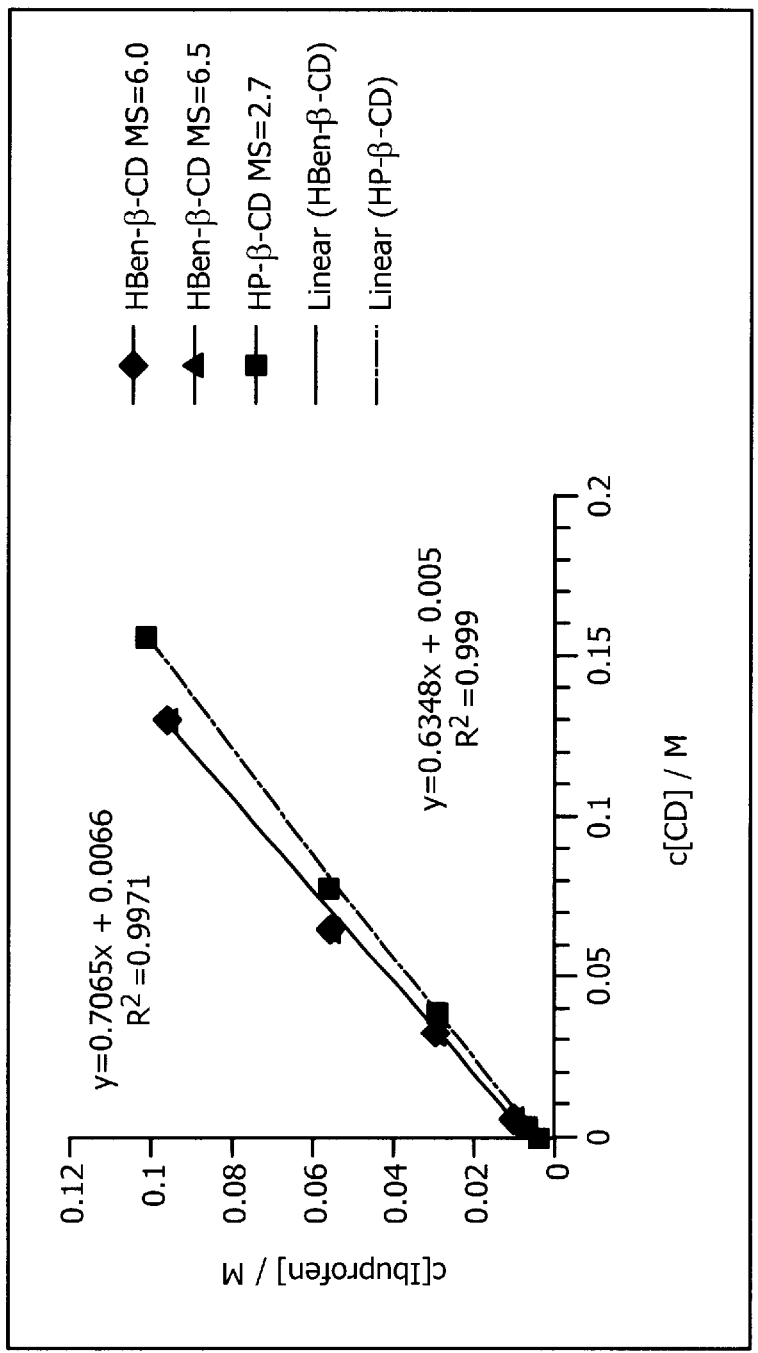
FIG. 8 shows the calculation of apparent binding constants for ibuprofen with MS 6.0 and 6.5 hydroxybutenyl-β-cyclodextrin (HBen-β-CD) and hydroxypropyl-β-cyclodextrin (HP-β-CD).
Figure 9:
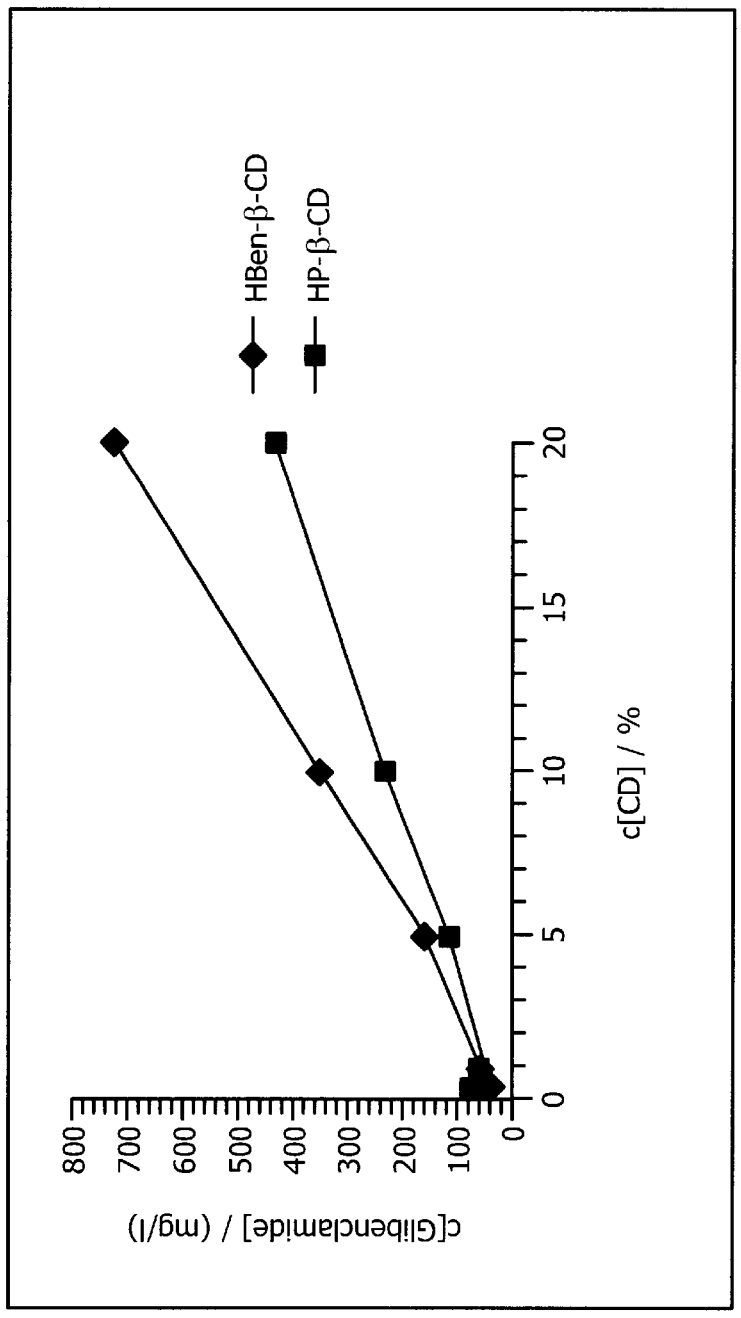
FIG. 9 shows the solubility isotherms of glibenclamide in an aqueous media in the presence of hydroxybutenyl-β-cyclodextrin (HBen-β-CD) and hydroxypropyl-β-cyclodextrin (HP-β-CD).
Figure 10:
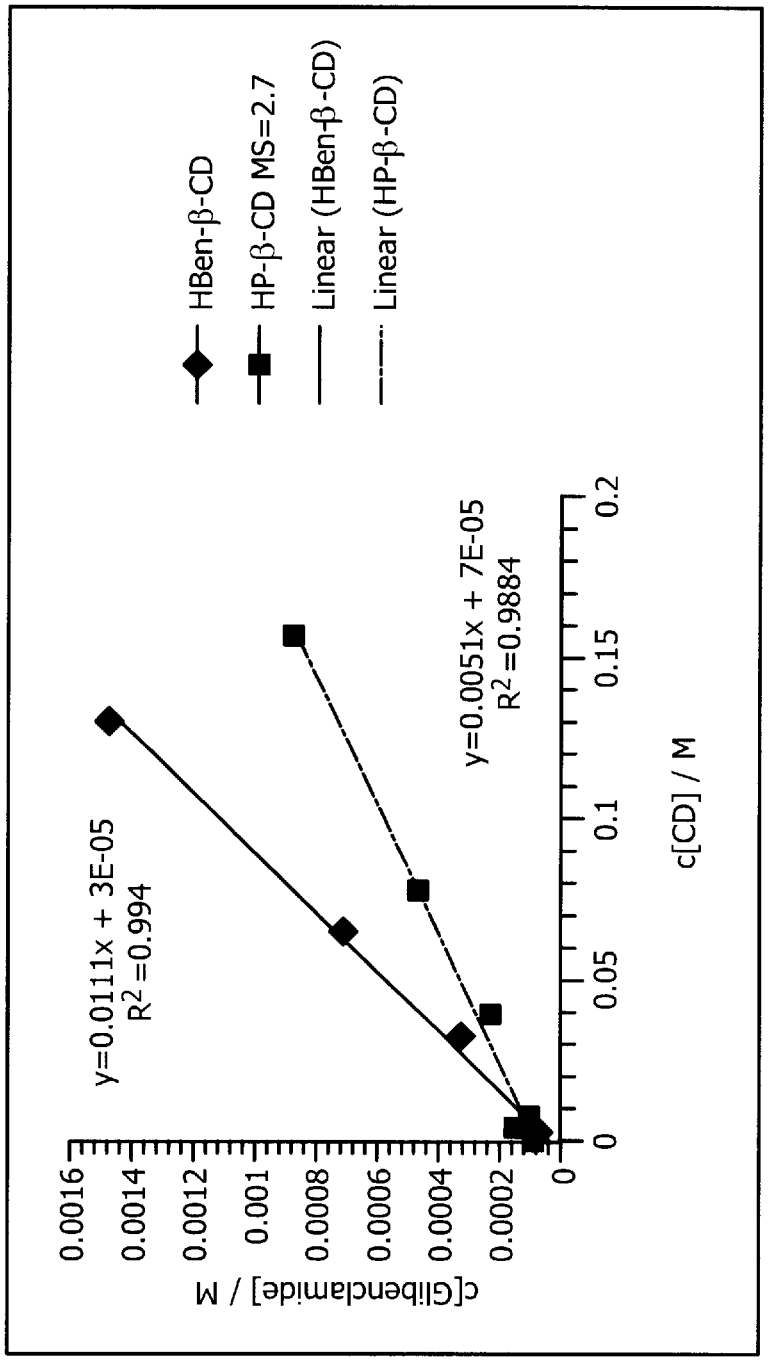
FIG. 10 shows the calculation of apparent binding constants for glibenclamide with hydroxybutenyl-β-cyclodextrin (HBen-β-CD) and hydroxypropyl-β-cyclodextrin (HP-β-CD).
Figure 11:
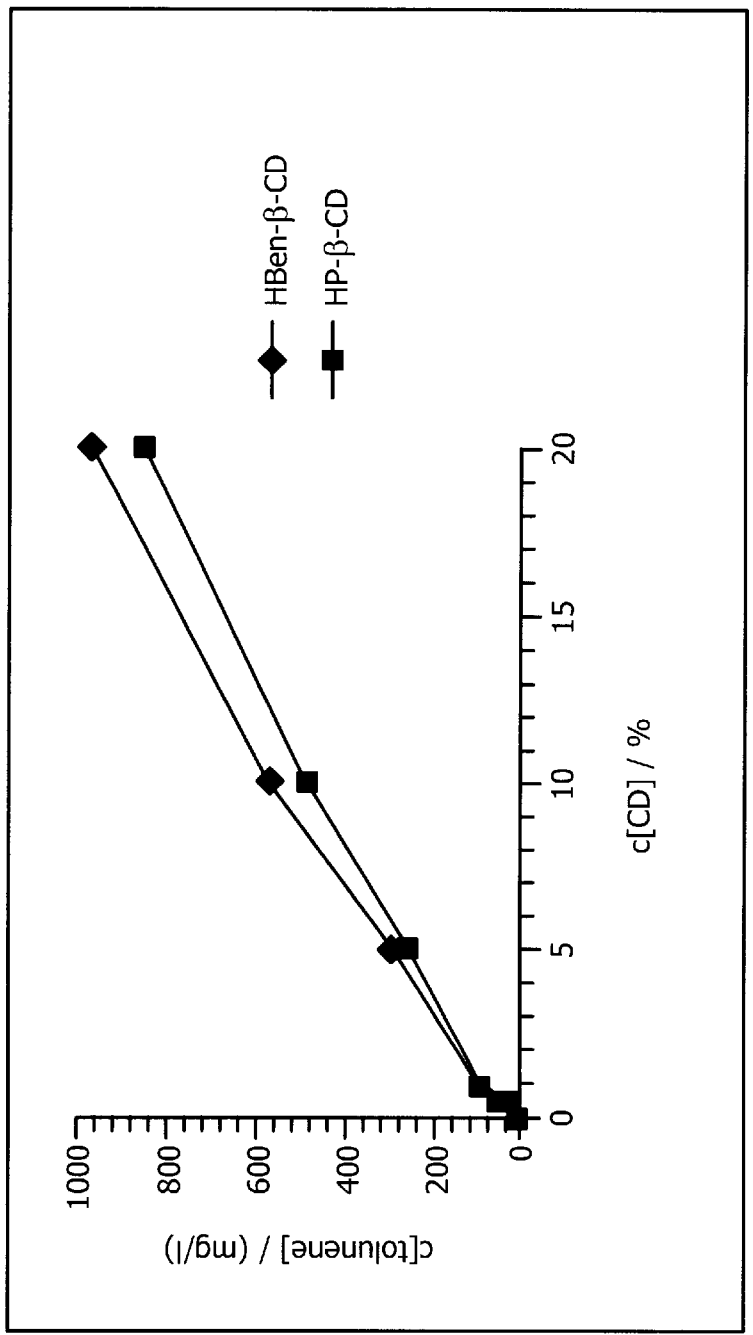
FIG. 11 shows the solubility isotherms of toluene in an aqueous media in the presence of hydroxybutenyl-β-cyclodextrin (HBen-β-CD) and hydroxypropyl-β-cyclodextrin (HP-β-CD).
Figure 12:
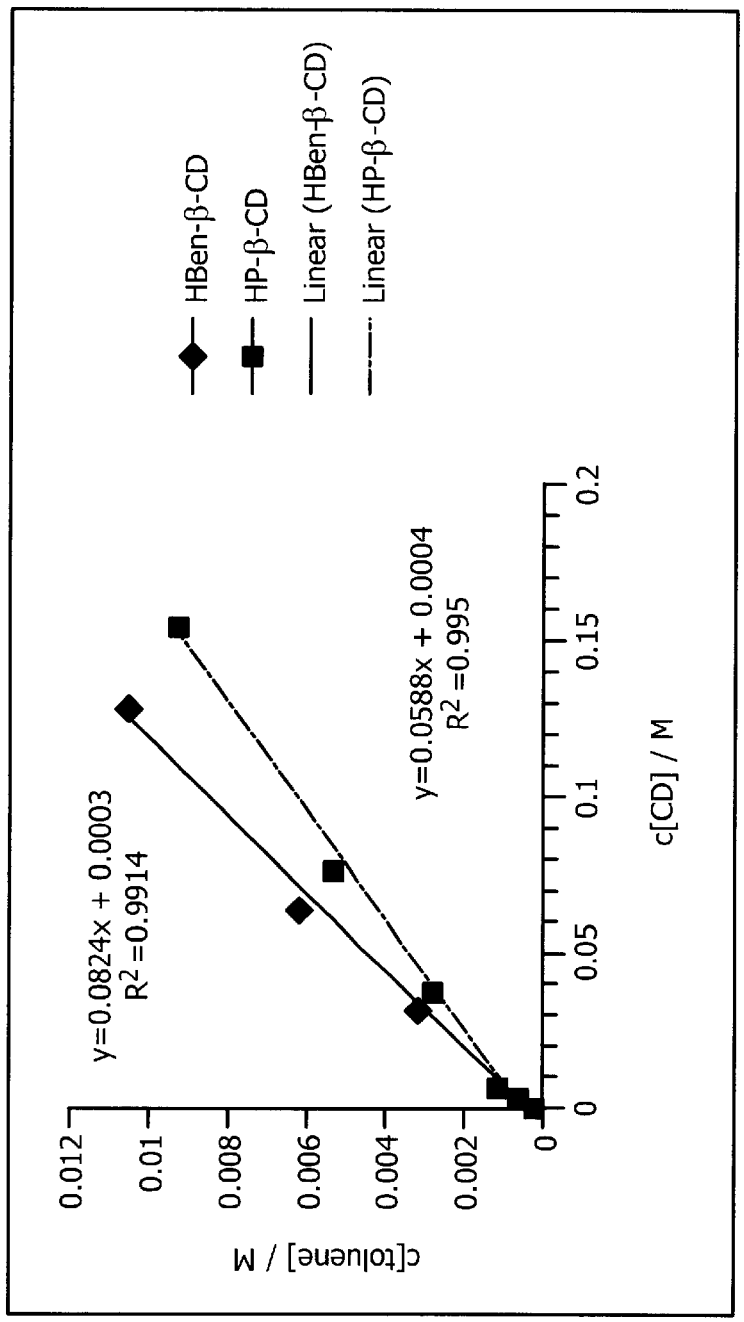
FIG. 12 shows the calculation of apparent binding constants for toluene with hydroxybutenyl-β-cyclodextrin (HBen-β-CD) and hydroxypropyl-β-cyclodextrin (HP-β-CD).
Figure 13:
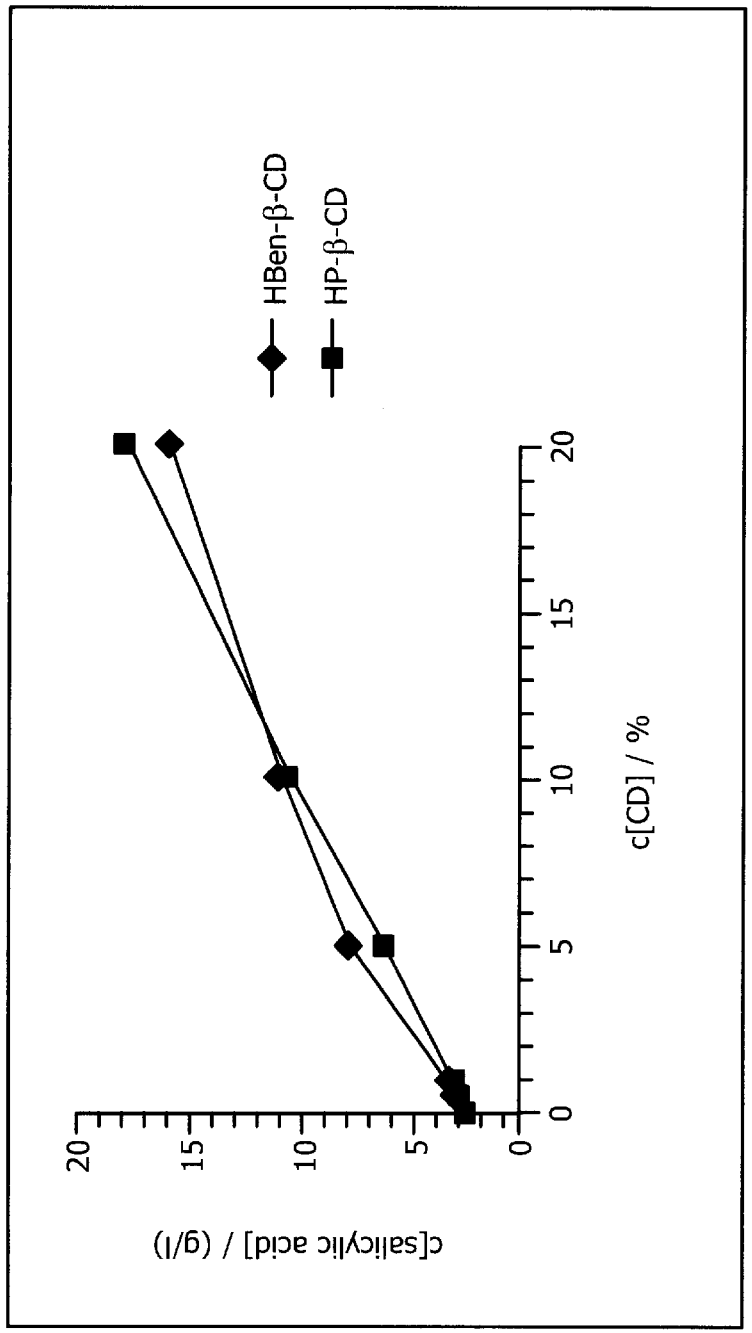
FIG. 13 shows the solubility isotherms of salicylic acid in an aqueous media in the presence of hydroxybutenyl-β-cyclodextrin (HBen-β-CD) and hydroxypropyl-β-cyclodextrin (HP-β-CD).
Figure 14:
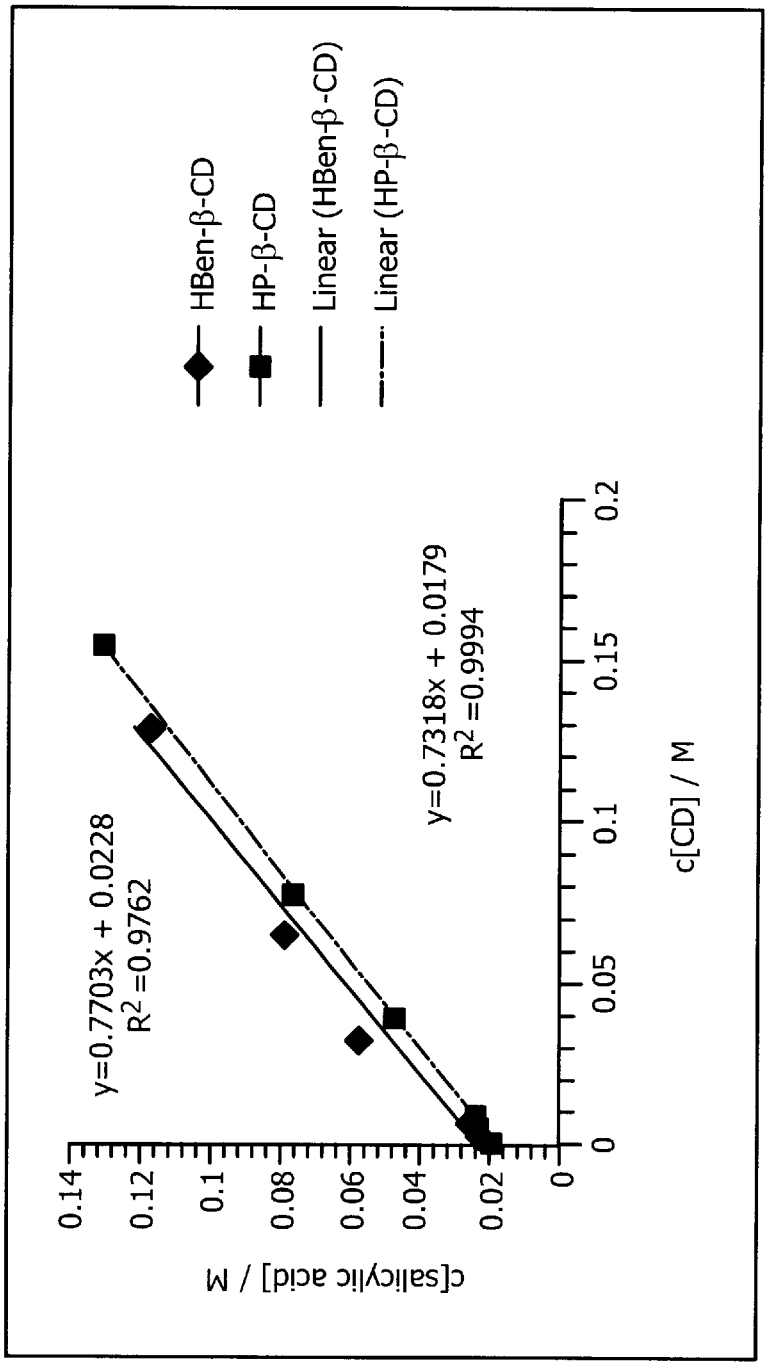
FIG. 14 shows the calculation of apparent binding constants for salicylic acid with hydroxybutenyl-β-cyclodextrin (HBen-β-CD) and hydroxypropyl-β-cyclodextrin (HP-β-CD).
Figure 15:
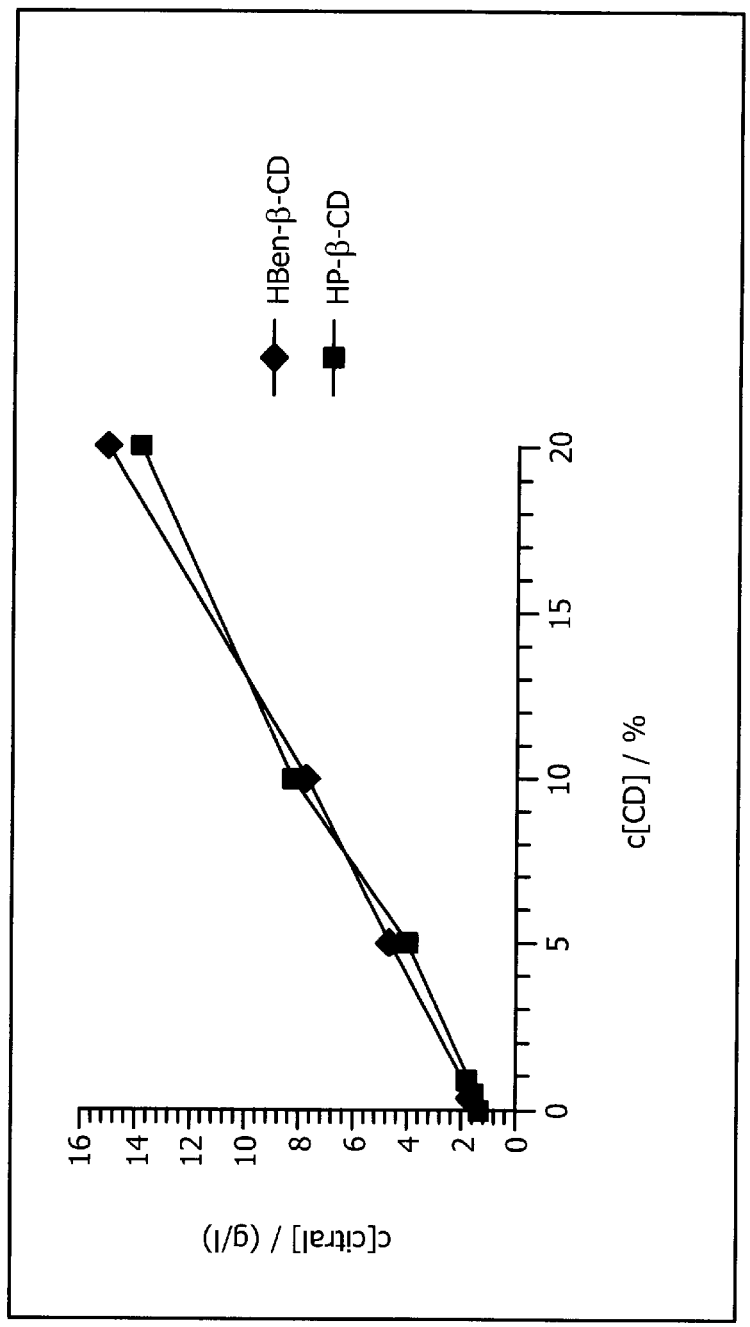
FIG. 15 shows the solubility isotherms of citral in an aqueous media in the presence of hydroxybutenyl-β-cyclodextrin (HBen-β-CD) and hydroxypropyl-β-cyclodextrin (HP-β-CD).
Figure 16:
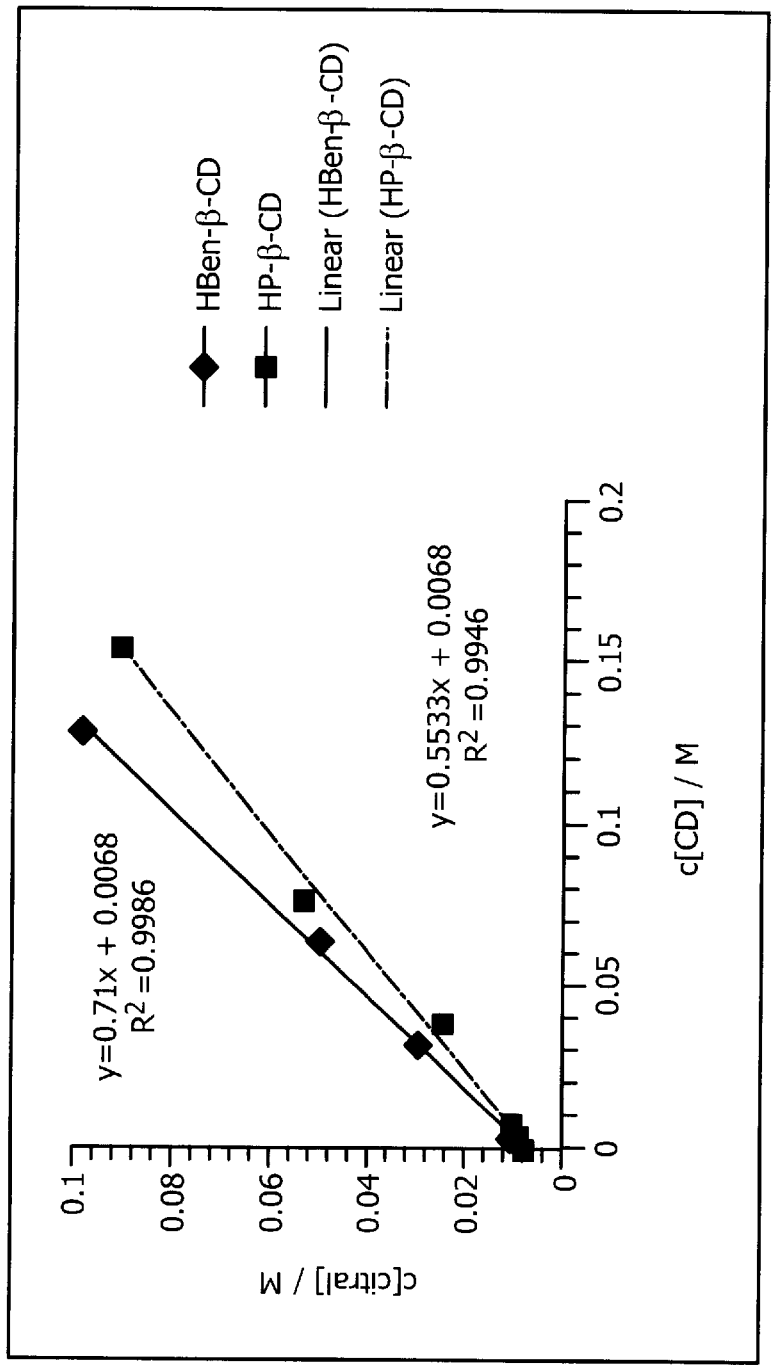
FIG. 16 shows the calculation of apparent binding constants for citral with hydroxybutenyl-β-cyclodextrin (HBen-β-CD) and hydroxypropyl-β-cyclodextrin (HP-β-CD).

Table 5 summarizes the apparent binding constants of HBen-β-CD and HP-β-CD as determined from the graphs in FIGS. 6, 8, 10, 12, 14 and 16. A higher binding constants indicates that the CD binds more effectively with the guest molecule. Significant differences could not be observed in complex forming ability between the two samples of HBen-β-CD (MS=6.5 and 6.0) (c.f. FIGS. 5 and 7, guest molecules were hydrocortisone and ibuprofen). With the exception of hydrocortisone, HBen-β-CD had higher binding constants than did HP-β-CD. In the case of the HBen-β-CD/hydrocortisone complex, the size of the binding constant indicates that HBen-β-CD binds very effectively with hydrocortisone.

TABLE 5

Apparent Binding Constants in Guest Molecule/CD Derivative Complexes.

| Material | $K_c$(HBen-β-CD)/$M^{-1}$ | $K_c$(HP-β-CD)/$M^{-1}$ |
|---|---|---|
| Hydrocortisone | 629 | 1373 |
| Ibuprofen | 520 | 376 |
| Glibenclamide | 136 | 62 |
| Toluene | 1111 | 773 |
| Salicylic Acid | 183 | 149 |
| Citral | 312 | 158 |

While the invention has been described with reference to preferred embodiments and working examples, it is to be understood that variations and modifications may be resorted to as will be apparent to those skilled in the art. Such variations and modifications are to be considered within the purview and scope of the invention as defined by the claims appended hereto.

We claim:

1. A solid cyclodextrin ether which comprises at least one hydroxybutenyl substituent.

2. The cyclodextrin ether according to claim 1, which comprises α-cyclodextrin, β-cyclodextrin, or γ-cyclodextrin.

3. The cyclodextrin ether according to claim 1, which has a degree of substitution (DS) ranging from about 0.02 to about 9.0.

4. The cyclodextrin ether according to claim 1, which has a degree of substitution (DS) ranging from about 1.0 to about 7.0.

5. The cyclodextrin ether according to claim 1, which has a degree of substitution (DS) ranging from about 9.0 to about 18–24.

6. The cyclodextrin ether according to claim 1, which has a degree of substitution (DS) ranging from about 12 to about 18–24.

7. The cyclodextrin ether according to claim 1, which has an average molar substitution of about 0.1 to about 7.

8. A solid cyclodextrin ether which comprises at least one hydroxybutenyl substituent and at least one R substituent where R arises from an O-alkylating agent other than hydroxybutenyl.

9. The cyclodextrin ether according to claim 8, which comprises α-cyclodextrin, β-cyclodextrin, or γ-cyclodextrin.

10. The cyclodextrin ether according to claim 8, wherein the O-alkylating agent is a lower alkylene oxide; an aryl or halogen substituted alkylene oxide; an alkyl-, hydroxyalkyl-, arylalkyl-, carboxyalkyl-, (alkyloxycarbonyl)alkyl-, allyl-, or vinyl-halide; a sulfonate; or mixtures thereof.

11. The cyclodextrin ether according to claim 8, wherein the O-alkylating agent is ethylene oxide, propylene oxide, butylene oxide, amylene oxide, glycidol, styrene oxide, epichlorohydrin, diazomethane, methyl chloride, methyl iodide, methyl bromide, ethyl bromide, propyl bromide, butyl bromide, propyl methyl sulfonate, methyl or ethyl chloroacetic acid, sodium chloroacetate, chloroacetic acid, benzyl bromide, 1-N,N-dialkylamino-2-chloroethane, or mixtures thereof.

12. The cyclodextrin ether according to claim 8, which has a degree of substitution (DS) ranging from about 0.02 to about 9.0.

13. The cyclodextrin ether according to claim 8, which has a degree of substitution (DS) ranging from about 1.0 to about 7.0.

14. The cyclodextrin ether according to claim 8, which has a degree of substitution (DS) ranging from about 9.0 to about 18–24.

15. The cyclodextrin ether according to claim 8, which has a degree of substitution (DS) ranging from about 12 to about 18–24.

16. The cyclodextrin ether according to claim 8, which has an average molar substitution of about 0.1 to about 7.

17. A water-soluble host molecule which comprises a solid hydroxybutenyl derivative of cyclodextrin, said host molecule having a degree of substitution (DS) of about 0.02 to about 9.0 and being capable of forming host-guest complexes.

18. The water-soluble host molecule according to claim 17, wherein the DS ranges from about 1.0 to about 7.0.

19. The water-soluble host molecule according to claim 17, which has an average molar substitution of about 0.1 to about 7.

20. A water-soluble host molecule which comprises a solid mixed ether of cyclodextrin where at least one ether substituent is hydroxybutenyl and at least one ether substituent is other than hydroxybutenyl, said host molecule having a degree of substitution (1)S) of about 0.02 to about 9.0 and being capable of forming host-guest complexes.

21. The water-soluble host molecule according to claim 20, wherein the DS ranges from about 1.0 to about 7.0.

22. The water-soluble host molecule according to claim 20, which has an average molar substitution of about 0.1 to about 7.

23. An inclusion complex which comprises:
(a) a water-soluble host molecule which comprises a solid hydroxybutenyl derivative of cyclodextrin, said host molecule having a degree of substitution (DS) of about 0.02 to about 9.0; and
(b) a guest molecule or a combination of guest molecules.

24. The inclusion complex according to claim 23, wherein the guest molecule is selected from the group consisting of anti-viral agents, anti-cancer agents, agents for treatment of neural disorders, anti-microbial and anti-fungal agents, steroids, non-steroid anti-rheumatic agents, cardiac glycosides, oligionucleotides, derivatives of benzodiazepine, benzimidazole, piperidine, piperazine, imidazole, and triazole.

25. The inclusion complex according to claim 23, wherein the guest molecule is selected from the group consisting of AZT, prostaglandin, ibuprofen, hydrocortisone, sodium loxoprofen, testosterone, piroxicam, benexate, iodine, dexamethasone, nitroglycerin, cefotiam hexetil HCl, thyaprofenic, chlordiazepoxide, itraconazole, garlic oil, and topiramate.

26. The inclusion complex according to claim 23, wherein said host molecule has an average molar substitution of about 0.1 to about 7.

27. An inclusion complex which comprises:
(a) a water-soluble lost molecule which comprises a solid mixed ether of cyclodextrin where at least one ether substituent is hydroxybutenyl and at least one ether substituent is other than hydroxybutenyl, said host molecule having a degree of substitution (DS) of about 0.02 to about 9.0; and
(b) a guest molecule or a combination of guest molecules.

28. The inclusion complex according to claim 27, wherein the guest molecule is selected from the group consisting of anti-viral agents, anti-cancer agents, agents for treatment of neural disorders, anti-microbial and anti-fungal agents, steroids, non-steroid anti-rheumatic agents, cardiac glycosides, oligionucleotides, derivatives of benzodiazepine, benzimidazole, piperidine, piperazine, imidazole, and triazole.

29. The inclusion complex according to claim 27, wherein the guest molecule is selected from the group consisting of AZT, prostaglandin, ibuprofen, hydrocortisone, sodium loxoprofen, testosterone, piroxicam, benexate, iodine, dexamethasone, nitroglycerin, cefotiam hexetil HCl, thyaprofenic, chlordiazepoxide, itraconazole, garlic oil, and topiramate.

30. The inclusion complex according to claim 27, wherein said host molecule has an average molar substitution of about 0.1 to about 7.

31. A water-insoluble host molecule which comprises a solid hydroxybutenyl derivative of cyclodextrin, said host molecule having a degree of substitution (DS) of about 9.0 to about 18–24 and being capable of forming host-guest complexes.

32. The water-insoluble host molecule according to claim 31, wherein the DS ranges from about 12 to about 18–24.

33. The water-insoluble host molecule according to claim 31, which has an average molar substitution of about 0.1 to about 7.

34. A water-insoluble host molecule which comprises a solid mixed ether of cyclodextrin where at least one ether substituent is hydroxybutenyl and at least one ether substituent is other than hydroxybutenyl, said host molecule having a degree of substitution (DS) of about 9.0 to about 18–24 and being capable of forming host-guest complexes.

35. The water-insoluble host molecule according to claim 34, wherein the DS ranges from about 12 to about 18–24.

36. The water-insoluble host molecule according to claim 34, which has an average molar substitution of about 0.1 to about 7.

37. An inclusion complex which comprises:
(a) a water-insoluble host molecule which comprises a solid hydroxybutenyl derivative of cyclodextrin, said host molecule having a degree of substitution (DS) of about 9.0 to about 18–24; and
(b) a guest molecule or a combination of guest molecules.

38. The inclusion complex according to claim 37, wherein the guest molecule is selected from the group consisting of fragrances, flavors, fungicides, antimicrobial agents, amines, diamines, deodorants, and insecticides.

39. The inclusion complex according to claim 37, wherein the guest molecule is selected from the group consisting of oils of sandalwood, lemon, Douglas fir, patchouli, strawberry, and vanilla, copper chloride, zinc salts, sodium bisulfite, EDTA, formaldehyde, isothiazolin, alanine, aspartic acid, cystine, glutamic acid, leucine, lysine, proline, serine, threonine, tryptophan, tyrosine, valine, derivatives of pyridine or aniline, 1,4-phenylenediamine, 1,2-diaminocyclohexane, 1,4-diaminobutane, 1,8-diaminooctane, and 2,4-diaminotoluene.

40. The inclusion complex according to claim 37, wherein said host molecule has an average molar substitution of about 0.1 to about 7.

41. An inclusion complex which comprises:
(a) a water-insoluble host molecule which comprises a solid mixed ether of cyclodextrin where at least one ether substituent is hydroxybutenyl and at least one ether substituent is other than hydroxybutenyl, said host molecule having a degree of substitution (DS) of about 9.0 to about 18–24; and
(b) a guest molecule or a combination of guest molecules.

42. The inclusion complex according to claim 41, wherein the guest molecule is selected from the group consisting of fragrances, flavors, fungicides, antimicrobial agents, amines, diamines, deodorants, and insecticides.

43. The inclusion complex according to claim 41, wherein the guest molecule is selected from the group consisting of oils of sandalwood, lemon, Douglas fir, patchouli, strawberry, and vanilla, copper chloride, zinc salts, sodium bisulfite, EDTA, formaldehyde, isothiazolin, alanine, aspartic acid, cystine, glutamic acid, leucine, lysine, proline, serine, threonine, tryptophan, tyrosine, valine, derivatives of pyridine or aniline, 1,4-phenylenediamine, 1,2-diaminocyclohexane, 1,4-diaminobutane, 1,8-diaminooctane, and 2,4-diaminotoluene.

44. The inclusion complex according to claim 41, wherein said host molecule has an average molar substitution of about 0.1 to about 7.

45. A thermoplastic shaped article which comprises from about 0.01 weight % to about 10 weight % of an inclusion complex comprising:
(a) a water-insoluble host molecule which comprises a solid hydroxybutenyl derivative of cyclodextrin, said host molecule having a degree of substitution (DS) of about 9.0 to about 18–24; and
(b) a guest molecule or a combination of guest molecules.

46. The thermoplastic shaped article according to claim 45, which comprises from about 1 weight % to about 5 weight % of the inclusion complex.

47. The thermoplastic shaped article according to claim 45, which comprises a thermoplastic material selected from the group consisting of polyolefins, aromatic polyesters, vinyl polymers, acrylic polymers, polynitriles, polyamides, aliphatic polyesters, aromatic-aliphatic copolyesters, $C_1$–$C_{10}$ esters of cellulose, polystyrene, polycarbonate, polylactates, polyhydroxybutyrates, polyhydroxybutyrate-valerate copolymers, polycaprolactone, cellophane and mixtures thereof.

48. The thermoplastic shaped article according to claim 45, which comprises a thermoplastic material selected from the group consisting of polyethylene, polypropylene, polyethylene-propylene copolymers, polyethylene terephthalate, polyethylene naphthalate, polyethylene terephthalate-naphthalate copolymers, polytetramethylene adipate-terephthalate copolymers, cellulose acetate, cellulose acetate propionate, cellulose acetate phthalate, cellulose acetate butyrate, cellulose propionate, cellulose butyrate, polylactic acid, polyvinyl chloride, polystyrene, polyethylene-vinyl acetate copolymers, polyethylene-vinyl alcohol copolymers and mixtures thereof.

49. The thermoplastic shaped article according to claim 45, wherein said host molecule has an average molar substitution of about 0.1 to about 7.

50. A thermoplastic shaped article which comprises from about 0.01 weight % to about 10 weight % of an inclusion complex comprising:
(a) a water-insoluble host molecule which comprises a solid mixed ether of cyclodextrin where at least one ether substituent is hydroxybutenyl and at least one ether substituent is other than hydroxybutenyl, said host molecule having a degree of substitution (DS) of about 9.0 to about 18–24; and
(b) a guest molecule or a combination of guest molecules.

51. The thermoplastic shaped article according to claim 50, which comprises from about 1 weight % to about 5 weight % of the inclusion complex.

52. The thermoplastic shaped article according to claim 50, which comprises a thermoplastic material selected from the group consisting of polyolefins, aromatic polyesters, vinyl polymers, acrylic polymers, polynitriles, polyamides, aliphatic polyesters, aromatic-aliphatic copolyesters, $C_1$–$C_{10}$ esters of cellulose, polystyrene, polycarbonate, polylactates, polyhydroxybutyrates, polyhydroxybutyrate-valerate copolymers, polycaprolactone, cellophane and mixtures thereof.

53. The thermoplastic shaped article according to claim 50, which comprises a thermoplastic material selected from the group consisting of polyethylene, polypropylene, polyethylene-propylene copolymers, polyethylene terephthalate, polyethylene naphthalate, polyethylene terephthalate-naphthalate copolymers, polytetramethylene adipate-terephthalate copolymers, cellulose acetate, cellulose acetate propionate, cellulose acetate phthalate, cellulose acetate butyrate, cellulose propionate, cellulose butyrate, polylactic acid, polyvinyl chloride, polystyrene, polyethylene-vinyl acetate copolymers, polyethylene-vinyl alcohol copolymers and mixtures thereof.

54. The thermoplastic shaped article according to claim 50, wherein said host molecule has an average molar substitution of about 0.1 to about 7.

* * * * *